United States Patent [19]

Bormann et al.

[11] 4,016,159
[45] Apr. 5, 1977

[54] ACYLAMINO-CEPHEM-CARBOXYLIC ACIDS CONTAINING AN AMIDINO OR GUANIDINO GROUP IN THE MOLECULE

[75] Inventors: Dieter Bormann; Bernd Knabe, both of Kelkheim, Taunus; Elmar Schrinner, Wiesbaden; Manfred Worm, Mainz, all of Germany

[73] Assignee: Hoechst Aktiengesellschaft, Frankfurt am Main, Germany

[22] Filed: Nov. 27, 1974

[21] Appl. No.: 527,704

[30] Foreign Application Priority Data

Nov. 29, 1973 Germany .......................... 2359544

[52] U.S. Cl. .................... 260/243 C; 260/256.4 H; 260/309.6; 260/518 R; 260/519; 424/246
[51] Int. Cl.[2] .............. C07D 501/56; C07D 501/48
[58] Field of Search ................. 260/243 C

[56] References Cited

UNITED STATES PATENTS 3,855,213  12/1974  Dunn et al. .................... 260/243 C
3,865,820  2/1975   Schorr et al. .................. 260/243 C

*Primary Examiner*—Nicholas S. Rizzo
*Assistant Examiner*—Diana G. Rivers
*Attorney, Agent, or Firm*—Curtis, Morris & Safford

[57] ABSTRACT

Acylamino-cephem-carboxylic acids of the formula I

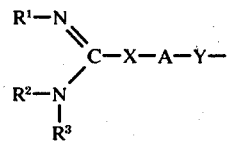

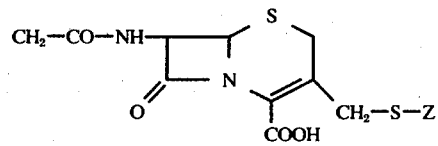

in which
R[1], R[2] and R[3] represent hydrogen or alkyl, R[1] and R[2] or R[2] and R[3] together may form an alkylene radical which may be substituted, X represents a single bond or NH, A represents a phenylene or thienylene radical which may be substituted, Y represents a single bond or oxygen and Z represents a 5- or 6-membered ring which may be substituted and which may be bound to an anellated ring system, and their physiologically tolerated salts and esters, a process for preparing these compounds and preparations containing them.

56 Claims, No Drawings

ACYLAMINO-CEPHEM-CARBOXYLIC ACIDS CONTAINING AN AMIDINO OR GUANIDINO GROUP IN THE MOLECULE

The present invention proves acylamino-cephem-carboxylic acids of the general formula I

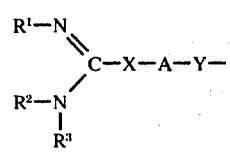

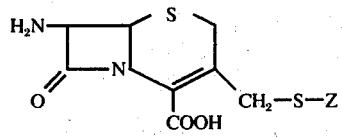

in which
$R_1$, $R_2$ and $R_3$ each represent hydrogen or alkyl radicals, $R_1$ and $R_2$ or $R_2$ and $R_3$ together may form an alkylene radical which may be substituted, X represents a single bond or NH, A represents a phenylene or thienylene radical which may be substituted, Y represents a single bond or oxygen and Z represents a 5- or 6-membered ring which may be substituted and which may also be bound to an anellated ring system, and their physiologically tolerated salts and esters.

The invention furthermore relates to a process for preparing the acylamino-cephem-carboxylic acids of the general formula I and their physiologically tolerated salts and esters, which comprises a. reacting 7-amino-Δ3-cephem-4-carboxylic acids of the general formula II, in which Z has the meaning given above,

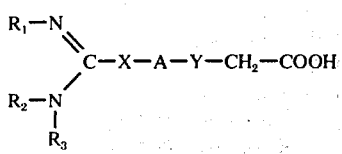

preferably in the form of their salts, or with a protected carboxyl group, with a carboxylic acid of the general formula III

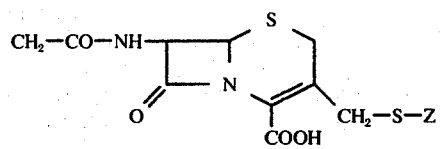

in which $R_1$, $R_2$, $R_3$, X, A and Y have the meanings given above, in particular in the form of a derivative capable of reacting with an amino group, or of a salt of such a compound, setting free the carboxyl group that may be protected and, if desired, converting the carboxylic acid obtained into a physiologically tolerated salt or a physiologically tolerated ester, or b. reacting acylamino-cephem-carboxylic acids of the general formula IV

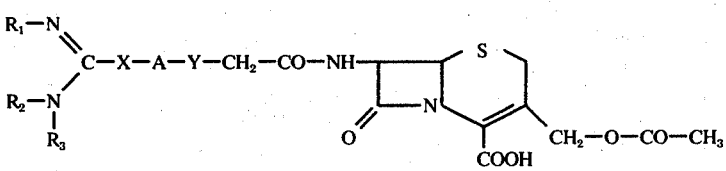

with mercapto compounds of the general formula V

Z — SH (V)

in which Z has the meaning given above.
and converting the products so obtained, if desired, into physiologically tolerated salts or esters.

If $R_1$, $R_2$ and $R_3$ represent an alkyl radical, they may be straight chain or branched alkyl radicals of 1 to 18, preferably 1 to 8 carbon atoms, the sum of the carbon atoms in the radicals $R_1$, $R_2$ and $R_3$ preferably not being greater than 16. As alkylene radicals, there may be used, for example those which contain 2 to 5, preferably 2 to 3 carbon atoms. As substituents of the alkylene radical, there may be mentioned, for example low molecular weight alkyl radicals containing 1 to 4 carbon atoms which themselves may be closed to a ring, preferably of 5 to 6 members, which may be interrupted by a hetero-atom, preferably an oxygen atom. The alkyl substituents of the akylene radical which are not closed to a ring may also contain a hetero-atom, preferably an oxygen atom.

Particularly suitable according to the invention are those compounds in which $R_1$, $R_2$ and $R_3$ are hydrogen or in which the radicals $R_1$ and $R_2$ represent an alkylene radical of 2 to 3 carbon atoms and $R_3$ represents hydrogen.

A represents, for example, the 1,2-phenylene, 1,3-phenylene and, in particular the 1,4-phenylene or the 2,5-thienylene radical; these radicals may also be substituted, for example by low molecular weight (1 to 4 carbon atoms) alkyl, alkoxy or halogen, preferably chlorine.

Preferably, A represents the unsubstituted 1,4-phenylene radical.

Z represents a 5- or 6-membered, preferably 5-membered, ring which may be substituted and which may consist of carbon atoms, but which preferably contains 1 to 4 hetero-atoms such as oxygen, sulfur and/or nitrogen as ring atoms. The radical Z may also be condensed with another ring system, for example to a benzene, pyridine or triazole ring, preferably to a benzene ring, the group Z which is not bound to a ring system being preferred. The ring system forming the radical Z may be hydrogenated completely or partially, preferably however not hydrogenated.

For the radical Z, there may be mentioned, for example the following basic ring systems: cyclopentyl, cyclohexyl, thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, thiazinyl, oxazinyl, triazinyl, thiadiazinyl, oxadiazinyl, dithiazinyl, dioxazinyl, oxathiozinyl, tetrazinyl, thiatriazinyl, oxatriazinyl, dithiadiazinyl, imidazolinyl and tetrahydropyrimidyl.

Among the ring systems cited above by way of example, there are preferably used 5-membered ring systems containing 1 to 2 nitrogen atoms and optionally 1 oxygen atom, for example oxazolyl, preferably oxazole-2-yl, oxadiazolyl, preferably 1,3,4-oxadiazole-5-yl, imidazolinyl, preferably imidazoline-2-yl, and 6-membered ring systems containing 1 to 3 nitrogen atoms and optionally 1 sulfur atom, for example pyridyl, such as pyride-2-yl, pyride-3-yl, pyride-4-yl, pyrimidyl, preferably pyrimide-2-yl and pyrimide-4-yl, tetrahydropyrimidyl, preferably 1,4,5,6-tetrahydropyrimide-2-yl, thiadiazinyl, in particular 4H-1,3,4-thiadiazine-2-yl, triazinyl, preferably 1,3,4-triazine-2-yl and 1,3,5-triazine-4-yl and pyridazinyl, in particular pyridazine-3-yl.

Particularly preferred are 5-membered ring systems containing 1 sulfur atom and 1 to 2 nitrogen atoms, for example thiazoylyl, in particular thiazole-2-yl, thiadiazolyl, in particular 1,3,4-thiadiazole-5-yl and 1,2,4-thiazole-5-yl, 5-membered ring systems containing 3 to 4 nitrogen atoms such as triazolyl, preferably 4H-1,2,4-triazole-3-yl and tetrazolyl, preferably 1H-tetrazole-5-yl.

The radical Z may be substituted once or several times by, for example:

alkyl groups containing, for example 1 to 15 carbon atoms such as methyl, ethyl, n-propyl, i-propyl, n-butyl, t-butyl, n-hexyl, undecyl and pentadecyl, preferably those containing 1 to 4 carbon atoms, in particular methyl.

Cycloalkyl groups, for example cyclopentyl and cyclohexyl, low molecular weight alkyl groups of 1 to 4 carbon atoms, preferably methyl, which are substituted, for example by aryl such as phenyl or thienyl, by aryloxy, for example phenoxy, by low molecular weight alkoxy, for example methoxy, ethoxy, by low molecular weight alkoxycarbonyl such as methoxy- or ethoxycarbonyl, or by halogen, low molecular weight alkoxy groups such as methoxy and ethoxy, low molecular weight alkenyl groups such as allyl, low molecular weight alkyl- and alkenyl-mercapto groups, for example methyl-mercapto and allyl-mercapto, low molecular weight alkoxycarbonyl, for example methoxycarbonyl, low molecular weight alkoxycarbonylamino, for example ethoxycarbonylamino, low molecular weight carboxyalkylthio, for example carboxymethylthio, amino, low molecular weight mono- and dialkylamino, for example methylamino, dimethylamino, ethylamino, diethylamino, oxido, hydroxy, nitro, cyano, halogen, preferably chlorine, mercapto, carboxy, aryl radicals, for example phenyl, substituted phenyl, for example low molecular weight alkoxyphenyl such as methoxyphenyl, ethoxyphenyl, halogenophenyl such as chlorophenyl, hydroxyphenyl, aminophenyl, alkyl phenyl, in particular low molecular weight alkylphenyl such as t-butylphenyl, tolyl, cetylphenyl, nitrophenyl, biphenylyl or pyridyl, methylpyridyl, furyl, naphthyl, quinolyl, isoquinolyl, thienyl, 2-thiazolyl, 2-pyrrolyl, 4-imidazolyl, 5-pyrazolyl and 4-isoxazolyl.

As radicals Z, there are preferred according to the invention those which are unsubstituted as well as those radicals Z which are substitited by alkyl, in particular low molecular weight alkyl, preferably methyl, and by aryl, in particular phenyl.

Special Examples of the radical Z are in particular the following radicals:

1H-1,2,3-Triazole-3-yl,
1,2,4-Triazole-3-yl,
5-Methyl-1,2,4-triazole-3-yl,
1-Phenyl-3-methyl-1H-1,2,4-triazole-5-yl,
4,5-Dimethyl-4H-1,2,4-triazole-3-yl,
5-Methyl-4-amino-4H-1,2,4-triazole-3-yl,
4-Phenyl-4H-1,2,4-triazole-3-yl,
5-Ethyl-1,2,4-triazole-3-yl,
4-Amino-4H-1,2,4-triazole-3-yl,
5-Ethyl-4-amino-4H-1,2,4-triazole-3-yl,
5-Phenyl-1,2,4-triazole-3-yl,
5-(4-Methoxyphenyl)-1,2,4-triazole-3-yl,
5-(4-Chlorophenyl)-1,2,4-triazole-3-yl,
5-(4-Pyridyl)-1,2,4-triazole-3-yl,
5-/4-(2-Methyl-pyridyl)/-1,2,4-triazole-3-yl,
5-Phenoxymethyl-1,2,4-triazole-3-yl,
5-Methoxymethyl-1,2,4-triazolo-3-yl,
5-Ethoxymethyl-1,2,4-triazole-3-yl,
5-Ethoxycarbonylmethyl-1,2,4-triazole-3-yl,
5-(2-Ethoxyethyl)1,2,4-triazole-3-yl,
5-(2-Aminoethyl)-1,2,4-triazole-3-yl,
4-Methyl-5-phenyl-4H-1,2,4-triazole-3-yl,
4-(4-Ethoxyphenyl)-5-(4-pyridyl)-4H-1,2,4-triazole-3-yl,
4-(4-Methoxyphenyl)-5-(4-pyridyl)-4H-1,2,4-triazole-3-yl,
4-(4-Ethoxyphenyl)-5-(3-pyridyl)-4H-1,2,4-triazole-3-yl,
4-(4-Ethoxyphenyl)-5-phenyl-4H-1,2,4-triazole-3-yl,
4-(4-Ethoxyphenyl)-5-(4-aminophenyl)-4H-1,2,4-triazole-3-yl,
4,5-Diphenyl-4H-1,2,4-triazole-3-yl,
4,5-Di-p-tolyl-4H-1,2,4-triazole-3-yl,
4-Allyl-5-phenyl-4H-1,2,4-triazole-3-yl,
4-Amino-5-methyl-4H-1,2,4-triazole-3-yl,
4-Amino-5-ethyl-4H-1,2,4-triazole-3-yl,
1-Methyl-5-phenyl-1,2,4-triazole-3-yl,
1-Phenyl-4-allyl-5-(m-nitrophenyl)-4H-1,2,4-triazole-3-yl,
1-Phenyl-4-allyl-5-t-butyl-4H-1,2,4-triazole-3-yl,
1H-Tetrazole-5-yl,
1-Methyl-1H-tetrazole-5-yl,
1-Ethyl-1H-tetrazole-5-yl,
1-n-Propyl-1-H-tetrazole-5-yl,
1-i-Propyl-1H-tetrazole-5-yl,
1-n-Butyl-1H-tetrazole-5-yl,
1-Cyclopentyl-1H-tetrazole-5-yl,
1-Phenyl-1H-tetrazole-5-yl,
1-p-Chlorophenyl-1H-tetrazole-5-yl,
1-Cyclohexyl-1H-tetrazole-5-yl,
1-Benzyl-1H-tetrazole-5-yl,
1-Allyl-1H-tetrazole-5-yl, 1,2,3-Thiadiazole-5-yl,
1,3,4-Thiadiazole-2-yl,
1,2,4-Thiadiazole-3-yl,
1,2,4-Thiadiazole-5-yl,
1,2,5-Thiadiazole-3-yl,
3-Methyl-1,2,4-thiadiazole-5-yl,
3-Phenyl-1,2,4-thiadiazole-5-yl,
2-Methyl-1,3,4-thiadiazole-5-yl,
2-Methylmercapto-1,3,4-thiadiazole-5-yl,
2-Ethyl-1,3,4-thiadiazole-5-yl, 2-n-Propyl-1,3,4-thiadazole-5-yl,
2-i-Propyl-1,3,4-thiadiazole-5-yl,
2-Phenyl-1,3,4-thiadiazole-5-yl,
2-(4-Methoxyphenyl)-1,3,4-thiadiazole-5-yl,
2-(4-Chlorophenyl)-1,3,4-thiadiazole-5-yl,
2-n-Heptyl-1,3,4-thiadiazole-5-yl,
2-(2Furyl)-1,3,4-thiadiazole-5-yl,
2-(3-(Pyridyl)1,3,4-thiadiazole-5-yl,
2-n-Butyl-1,3,4-thiadiazole-5-yl,
2-(2-Pyridyl)1,3,4-thiadiazole-5-yl,
2-(4-Pyridyl)-1,3,4-thiadiazole-5-yl,
2-(1-Naphthyl)1,3,4-thiadiazole-5-yl,
2-(2-Quinolyl)-1,3,4-thiadiazole-5-yl,
2-(1-Isoquinolyl)-1,3,4-thiadiazole-5-yl,
2-Ethoxycarbonylmethyl-1,3,4-thiadiazole-5-yl,
2-Phenyl-3-methyl-1,3,4-thiadiazole-5-yl,
2-Ethoxycarbonylamino-4-methyl-1,3,4-thiadiazole-5-yl,
3-Methylmercapto-1,3,4-thiadiazole-5-yl, 1,2,4-Oxadiazole-5-yl,
1,2,3-Oxadiazole-5-yl,
1,3,4-Oxadiazole-5-yl,
2-Methyl-1,3,4-oxadiazole-5-yl,
2-Ethyl-1,3,4-oxadiazole-5-yl,
2-Phenyl-1,3,4-oxadiazole-5-yl,
2-(4-Nitrophenyl)-1,3,4-oxadiazole-5-yl,
2-(2-Thienyl)-1,3,4-oxadiazole-5-yl,
2-(3-Thienyl)-1,3,4-oxadiazole-5-yl,
2-(4-Chlorophenyl)-1,3,4-oxadiazole-5-yl,
2-(2-Thiazolyl)-1,3,4-oxadiazole-5-yl,
2-(2-Furyl)-1,3,4-oxadiazole-5-yl,
2-(4-Pyridyl)-1,3,4-oxadiazole-5-yl,
2-(3-Nitrophenyl)-1,3,4-oxadiazole-5-yl,
2-(2-Methoxyphenyl)-1,3,4-oxadiazole-5-yl,
2-(2-Tolyl)-1,3,4-oxadiazole-5-yl,
2-(3-Tolyl)-1,3,4-oxadiazole-5-yl,
2-(2-Hydroxyphenyl)-1,3,4-oxadiazole-5-yl,
2-(4-Hydroxyphenyl)-1,3,4-oxadiazole-5-yl,
2-n-Butyl-1,3,4-oxadiazole-5-yl,
2-n-Propyl-1,3,4-oxadiazole-5yl,
2-Benzyl-1,3,4-oxadiazole-5-yl,
2-(1-Naphthyl)-1,3,4-oxadiazole-5-yl,
2-(2-Pyrrolyl)-1,3,4-oxadiazole-5-yl,
2-(4-Imidazolyl)-1,3,4-oxadiazole-5-yl,
2-(5-Pyrazolyl)-1,3,4-oxadiazole-5-yl,
2-(3,5-Dimethyl-4-isoxazolyl)-1,3,4-oxadiazole-5-yl, Thiazole-2-yl,
4-Methyl-thiazole-2-yl,
4-Phenyl-thiazole-2-yl,
4-Pentyl-thiazole-2-yl,
4-Hexyl-thiazole-2-yl,
4-Undecyl-thiazole-2-yl,
4-Tridecyl-thiazole-2-yl,
4-Pentadecyl-thiazole-2-yl,
4-p-t-Butylphenyl-thiazole-2-yl,
4-p-Cetylphenyl-thiazole-2-yl,
4-p-Phenylphenyl-thiazole-2-yl,
4-Ethyl-thiazole-2-yl,
4,5-Dimethyl-thiazole-2-yl,
Benzthiazole-2-yl, 4,5-Dimethyl-oxazole-2-yl,
4-Phenyl-oxazole-2-yl,
Benzoxazole-2-yl,
Oxazoline-2-yl, Imidazole-2-yl,
Imidazoline-2-yl,
Benzimidazoline-2-yl,
1-Methyl-imidazoline-2-yl, 2-Furyl,
2-Thiophenyl,
2-Pyrrolyl,
2-Thiazolinyl,
3-Isoxanolyl,
3-Pyrazolyl,
Thiatrizole-5-yl,
Purinyl,
Pyride-2-yl,
Pyride-3-yl,
Pyride-4-yl,
5-Nitropyride-2-yl,
1-Oxidopyride-2-yl Pyrimide-2-yl,
1,4,5,6-Tetrahydropyrimide-2-yl,
4-Hydroxy-pyrimide-2-yl,
4-Hydroxy-6-methyl-pyrimide-2-yl,
2-Hydroxy-pyrimide-2-yl,
2-Phenyl-5-ethoxycarbonyl-6-methyl-pyrimide-4-yl,
2-Phenyl-5-ethoxycarbonyl-6-ethoxy-pyrimide-4-yl,
2-Phenyl-5-ethoxycarbonyl-6-amino-pyrimide-4-yl,
2-Hydroxy-5-cyano-6-methyl-pyrimide-4-yl,
2,6-Dimethyl-5-acetyl-pyrimide-4-yl,
2-Undecyl-5-acetyl-6-methyl-pyrimide-4-yl,
2,6-Dimethyl-5-ethoxycarbonyl-pyrimide-4-yl,
Triazolopyridyl,
Pyridazinyl,
Pyrazinyl,
2-Methylmercapto-6-phenyl-1,3,5-triazine-4-yl,
5-Methyl-6-hydroxy-1,3,4-triazine-2-yl,
5-Phenyl-4H-1,3,4-thiadiazine-2-yl,
5-Hydroxy-4H-1,3,4-thiadiazine-2-yl, In the acylation of the amino-cephem acids of the general formula II, there may be used as starting materials, for example the following compounds of the formula III:

4-Amidinophenylacetic acid,
4-N-Methyl-amidino-phenylacetic acid,
4-N,N-Dimethyl-amidino-phenylacetic acid,
4-N,N'-Dimethylamidino-phenylacetic acid,
4-N,N,N'-Trimethyl-amidino-phenylacetic acid,
4-N-Ethyl-amidino-phenylacetic acid,
4,N,N'-Dipropyl-amidino-phenylacetic acid,
4-N,N'-Di-n-octyl-amidino-phenylacetic acid,
4-N-i-Pentyl-amidino-phenylacetic acid,
4-N,N-Dimethyl-N'-ethylamidino-phenylacetic acid,
4-(2-Imidazolinyl)-phenylacetic acid,
4-(1,4,5,6-Tetrahydro-2-pyridmidyl)-phenylacetic acid,
4-(1-Methyl-1,4,5,6-tetrahydro-2-pyrimidyl)-phenylacetic acid,
4-[5,5-Bis-(2-methoxy-ethyl)-1,4,5,6-tetrahydro-2-pyrimidyl]-phenylacetic acid,
4-(1,5-Dimethyl-2-imidazolinyl)-phenylacetic acid,
4-(1-Methyl-5-butyl-2-imidazolinyl)-phenylacetic acid,
4-(5,5-Dimethyl-1,4,5,6-tetrahydro-2-pyrimidyl)-phenylacetic acid,
4-(1,4,6,7,8,9-Hexahydro-5H-cyclopentenyl[d-]pyrimidyl-2)-phenylacetic acid, 4-(9-Oxa-2,4-diazaspiro[5,5]undec-2-en-3-yl)-phenylacetic acid,
4-(2,4-Diazaspiro[5,5]-undec-2-en-3-yl)-phenylacetic acid,
4-N,N'-Tetramethylene-amidino-phenylacetic acid,
3-Amidino-phenylacetic acid,
4-Amidino-2-methyl-phenylacetic acid,
4-Amidino-2-methoxy-phenylacetic acid,
4-Amidino-2-butoxy-phenylacetic acid,
4-Amidino-2-chloro-phenylacetic acid,
4-N,N-Pentamethylene-amidino-phenylacetic acid or the corresponding phenoxy-, thienyl- or thienyloxy-acetic acids, or the corresponding acids of the formula II with X = NH.

The carboxylic acids of the general formula III, in which X represents a single bond, are prepared in known manner starting from cyano-phenyl-, cyano-phenoxy- or cyanothienyl- or cyanothienyloxy-acetic acid esters. After conversion of the nitrile group into an imino ether, the latter is reacted with ammonia or an amine or diamine to the amidine and finally the carboxylic ester group or an acid amide group formed from it is hydrolyzed (Houben-Weyl 8, 697).

The carboxylic acid of the general formula III in which X = NH is prepared in known manner from the corresponding aminocarboxylic acids or aminocarboxylic acid derivatives by reacting the amino group of these compounds with cyanamides, carbodiimides, thioureas, S-alkyl-isothioureas, O-alkyl-isoureas or similar substances, which may be substituted (Houben-Weyl 8, 180 or 195). On the other hand, it is also possible to react the amino group of the above-mentioned aminocarboxylic acid derivatives in known manner (Houben-Weyl 9, 887) to thioureas or S-alkyl-isothioureas and react the latter with amines to the carboxylic acids of the general formula III in which X = NH.

The preparation of the 7-amino-Δ3-cephem-4-carboxylic acids of the general formula II is described, in principle, for example in the Netherland Pat. No. 7,005,519, Belgian Pat. No. 759,570 or Japanese Pat. No. 7 135 751; it is effected by reaction of 7-aminocephalosporanoic acid (7-ACS) with mercapto-heterocycles Z — SH.

The novel acyl derivatives of 7-amino-Δ3-cephem-4-carboxylic acids of the general formula II are obtained according to method (a) in a particularly advantageous manner by reacting the 7-amino-Δ3-cephem-4-carboxylic acids of the general formula II in the form of a salt, in particular of an alkali metal salt or tertiary amine salt, for example the sodium, potassium or triethylamine salt, with a reactive derivative of a carboxylic acid of the general formula III.

The salts of the 7-amino-Δ3-cephem-4-carboxylic acids of the general formula II may be used directly or they may be prepared in the solution used for the reaction from 7-amino-Δ3-cephem-4-carboxylic acids of the general formula II and, for example sodium bicarbonate, di-sodium hydrogenphosphate or triethylamine.

For the acylation of the 7-amino-Δ3-cephem-4-carboxylic acids of the general formula II of the invention, there have proved as reactive derivatives of the carboxylic acids of the general formula III in particular the acid chlorides. They may be prepared in known manner from the carboxylic acids by the action of thionyl chloride in an inert solvent, for example an aromatic hydrocarbon. They are then obtained in the form of hydrochlorides which may be used directly for the further reaction. In addition to the acid chlorides, also other reactive derivatives of the carboxylic acids of the formula III, for example acid bromides, activated esters such as the p-nitrophenyl ester, p-nitrophenyl-thio ester or the cyanomethyl ester, acid azides, acid cyanides or symmetrical or mixed anhydrides may be used. It is also possible to use reactive addition compounds of the carboxylic acids of the general formula III, and, for example, the carbodiimides which act as condensation agents, the 7-amino-Δ3-cephem-4-carboxylic acids of the general formula II being used advantageously with a protected carboxyl group, thus, for example in the form of a salt or an ester. The reactive derivatives may be used not only in the form of the hydrochlorides, but also in the form of other salts which are obtained, for example during preparation, for example in the form of the hydrobromide or acetate.

The acylation of the 7-amino-Δ3-cephem-4-carboxylic acid is advantageously effected by adding equimolar amounts or a slight excess of a compound of the formula III in the form of its reactive derivative to the solution of a salt of the 7-amino-Δ3-cephem-4-carboxylic acid in water or in a mixture of water and a solvent which is miscible with water, for example acetone, dimethylformamide, dimethylacetamide, dioxane or tetrahydrofurane, at an as far as possible neutral pH-value, preferably at pH-value of 6 to 9. It has particularly well proved to introduce the hydrochloride of the acid chloride in solid form. In order to bind the hydrochloric acid, two equivalents of a base, for example sodium bicarbonate or triethylamine, are previously added to the solution. The reaction is carried out at room temperature or at slightly reduced temperatures, preferably at temperatures in the range of from −5° and +5° C. The pH-value which, is at first weakly alkaline, falls during the reaction to about 7.

The 7-amino-Δ3-cephem-4-carboxylic acids of the general formula II may also be used with a protected carboxyl group, in particular in the form of their esters.

In the ester group (—COOR), the following radicals may be ued for R, for example:

straight chain or branched alkyl, cycloalkyl, aryl, aralkyl, aryloxyalkyl, alkoxyalkyl, acyloxyalkyl, aroylalkyl, which may be substituted, a heterocyclic radical or the silyl radical.

If the ester radical R has the meaning of straight chain or branched alkyl, there may be used in particular alkyl of 1 to 12 carbon atoms, preferably 1 to 5 carbon atoms, especially methyl and tert. butyl. As substituents, there may be mentioned, for example, halogen atoms, preferably chlorine and iodine. Corresponding substituents would be, for example 2,2,2-trichloroethyl or -2-iodoethyl. As cycloalkyl radicals, there may be used in particular those containing 5 to 10 carbon atoms, for example cyclohexyl, in particular isobornyl or adamantyl. As aryl radicals, there may be mentioned in particular phenyl, as aralkyl radicals those containing low molecular alkyl, in particular benzyl or benzhydryl which may be substituted by low molecular alkoxy or nitro groups. As examples, there may be mentioned p-methoxybenzyl or p-nitrobenzyl. As aryloxyalkyl and alkyloxyalkyl groups, there may be used in particular those containing low molecular weight alkyl groups, preferably phenoxymethyl or methoxymethyl. Among the acyloxyalkyl groups those are of interest which contain low molecular weight acyl and alkyl, for example acetoxymethyl, pivaloyloxymethyl or phthalyl. Among the aroylalkyl groups containing low molecular weight alkyl, there may be mentioned, for example benzoylmethyl and, as example of a heterocyclic radical, the thienyl radical.

As silyl radicals, low molecular weight radicals are of particular interest, for example trimethylsilyl.

Preferred esters are those which can be split under relatively mild conditions. for example hydrogenolytically, by hydrolysis, or enzymatically, for example the benzhydryl ester, the benzyl ester, the 4-methoxybenzyl ester, the 4-nitrobenzyl ester, the t-butyl ester, the trichloroethyl ester, the acetoxymethyl ester, the pivaloyloxymethyl ester, the 3-phthalide ester or the trimethylsilyl ester.

The esters of the 7-amino-$\Delta 3$-cephem-4-carboxylic acids of the general formula II can be prepared, for example, by des-acylation of corresponding 7-acylamino-cephem-carboxylic acid esters. The des-acylation is effected by reacting the acylated esters with a silylation agent in the presence of a base and converting them with phosphorus pentachloride into a complexlike compound, subsequently converting the amide group, which has been activated by the silylation, by the addition of a halogenating agent into the imino halide, reacting the latter with an alcohol to an imino ether and hydrolyzing.

The basic cephem-carboxylic acids of the general formula I are obtained in the form of inner salts and crystallize in most cases directly and may be isolated by suction-filtration. In some cases, they have to be precipitated from a non-solvent, for example acetone, and, for purification, recrystallized or dissolved and reprecipitated from suitable solvent mixtures.

Method (b) for preparing the acylamino-cephem-carboxylic acids of the general formula I of the invention comprises reacting acylamino-cephem-carboxylic acids of the general formula IV with the above-specified mercapto compounds of the general formula V. The compounds of the general formula IV required for this purpose may be obtained according to the process described in DOS No. 2,118,635. They are prepared by acylation of 7-aminocephalosporanoic acid with the above-mentioned acids of the general formula III.

Method (b) is preferably carried out in water or in organic solvents or mixtures of water and organic solvents. As organic solvents, there may be used, for example acetone, N,N-dimethylformamide, N,N-dimethylacetamide, tetrahydrofurane and acetonitrile. The reaction temperature may be varied within a wide range; the preferred temperature is about 20° to 120° C, but it is particularly preferred to operated in the temperature range of from about 40° to 80° C.

The reaction time depends considerably on the temperature and is at, for example 60° to 80° C about 3 to 1 hours.

The reaction according to (b) succeeds in a large pH-range; in order to obtain high yields, however, it is advisable to operate in a pH-range of from about 3 to 9; particularly preferred is the pH-range of from 6 to 7.5. To maintain the optimum pH-value constant, it is suitable to add weak bases, for example sodium bicarbonate or to operate in buffer mixtures, for example sodium hydrogenophosphate/disodium hydrogenophosphate.

In order to obtain particularly high yields, it is advisable to carry out the reaction under an inert protective gas, for example nitrogen or argon.

Isolation of the final products of the general formula I may be carried out in various ways, for example by filtration of the crystallized products or by concentration of the reaction solution and separation of the sideproducts by various solvents.

The novel acylamino-cephem-carboxylic acids of the general formula I contain in the molecule an amidino or guanidino group which may be substituted and, therefore, have amphoteric nature. They form inner salts and are soluble in water with a pH-value of about 5.

If according to method (a) an ester is obtained, it may be split, for example by hydrogenolysis (for example, the benzyl or p-nitrobenzyl ester) or other estersplitting agents, for example by trifluoroacetic acid (for example the tert.butyl ester), mixture of trifluoroacetic acid and anisole (for example, the benzhydryl ester, the 4-methoxy-benzyl ester).

The products of the invention, of the formula I may be used as such or in the form of their physiologically tolerated salts or esters. Such physiologically tolerated salt formers are, for example hydrochloric acid, sulfuric acid, nitric acid, toluene-sulfonic acid, methane-sulfonic acid, hyrobromic acid, amidosulfonic acid, citric acid or acetic acid. Strong acids are preferred as salt formers. The salt formation is effected, for example, by combination of equivalent amounts of a compound of the formula I and the acid in solution and evaporation.

If carboxylic acids of the formula I obtained according to (a) or (b) are to be converted into physiologically tolerated esters, this can be carried out according to methods known from literature, for example by the reaction with aliphatic diazo compounds. It is preferred to prepare physiologically tolerated esters of the acids of the general formula I according to method (a) using the corresponding esters of the acids of the general formula II.

The novel acylamino-cephem-carboxylic acids of the general formula I have outstanding antibacterial properties. Their action against gram-positive and gram-negative germs is comparable to that of penicillins. In addition thereto, they have the advantage of a good activity against penicillinase-forming streptococci (Table 1).

Table 1

| Minimum inhibition concentration (MIC) in γ/ml Germ: Staphylococcus aureus 285 | |
|---|---|
| Substance | MIC |
| Penicillin-G-Na | 125 |
| Penicillin-V-K | 125 |
| Ampicillin | 100 |
| Examples | |
| 1, 2, 3, 4, 5, 6, 12, 26, 28, 31, 32, 33 25, 38, 40, 44, 45, 47, 48, 50, 51, 52, 54, 55, 56, 57, 58, 63, 65, 69, 70, 80, 85, 89, 90, 91, 92, 103, 105, 106, 108, 111, 112, 113, 114, 118, 120, 121, 127, 128, 129, 130, 109 | 0.156–0.391 |
| Examples | |
| 7, 8, 9, 10, 11, 14, 18, 19, 22, 24, 25, 27, 29, 30, 34, 37, 39, 41, 46, 49, 53, 59, 60, 61, 62, 64, 66, 67, 68, 71, 73, 74, 75, 76, 77, 78, 79, 82, 83, 98, 99, 101, 116, 117, 122, 124, 126 | 0.5–1.25 |
| Examples | |
| 15, 16, 17, 23, 81, 87, 94, 95, 97, 102, 104, 107, 115, 123 | 1.6–2.5 |

Compared to the commercial cephalosporins, the novel acylamino-cephem-carboxylic acids of the general formula I have a partly better activity against gram-negative germs (Table 2) and an essentially better action against gram-positive germs (Tables 3, 4 and 5).

Table 2

Minimum inhibition concentration (MIC) in /ml
Germ: Proteus mirabilis

| Substance | MIC |
|---|---|
| Cephalotin-Na | 12.5 |
| Cephalexin | 25 |
| Cephazolin-Na | 25 |
| Examples | |
| 1, 3, 6, 11, 12, 18, 19, 22, 25, 44, 58, 60, 70, 89, 100, 120, 124 | 3.1–12.5 |
| Examples | |
| 2, 4, 9, 23, 24, 53, 55, 94, 97, 101, 107, 118, 121 | 25 |

Table 3

Minimum inhibition concentration MIC in γ/ml
Germ: Streptococcus pyogenes A

| Substance | MIC |
|---|---|
| Cephalotin-Na | 0.05 |
| Cephalexin | 0.156 |
| Cephazolin-Na | 0.03 |
| Examples | |
| 1, 4, 9, 10, 19, 25, 26, 27, 28, 29, 30, 31, 32, 33, 35, 37, 41, 44, 45, 46, 50, 51, 52, 53, 54, 55, 56, 57, 58, 59, 60, 64, 65, 69, 70, 71, 73, 75, 80, 83, 85, 90, 91, 92, 97, 98, 103, 105, 106, 108, 109, 111, 112, 113, 114, 115, 116, 117, 118, 120, 121, 127 | 0.000391–0.0078 |
| Examples | |
| 2, 3, 6, 11, 12, 14, 18, 22, 34, 38, 39, 40, 47, 61, 63, 62, 66, 68, 74, 77, 78, 79, 81, 82, 89, 94, 95, 99, 100, 102, 122, 124, 126, 128, 129, 130 | 0.008–0.0156 |

Table 4

Minimum inhibition concentration (MIC) in γ/ml
Germ: Streptococcus D

| Substance | MIC |
|---|---|
| Cephalotin-Na | 78.5 |
| Cephalexin | 100 |
| Cephazolin | 100 |
| Examples | |
| 12, 33, 34, 37, 48, 50, 51, 52, 53, 70, 92, 111, 112, 113, 114, 118 | 0.196–6.25 |
| Examples | |
| 1, 2, 3, 4, 5, 6, 7, 8, 9, 10, 11, 14, 15, 16, 17, 18, 19, 22, 25, 26, 27, 28, 29, 30, 31, 32, 35, 38, 39, 41, 44, 45, 46, 47, 49, 54, 55, 56, 57, 58, 59, 60, 61, 62, 63, 64, 65, 68, 69, 71, 73, 75, 76, 79, 80, 81, 82, 83, 85, 89, 93, 94, 95, 97, 98, 99, 102, 103, 105, 106, 107, 108, 115, 116, 117, 109, 120, 121, 122, 124, 126 | 10–50 |

Table 5

Minimum inhibition concentration (MIC) in γ/ml
Germ: Staphylococcus aureus SG 511

| Substance | MIC |
|---|---|
| Cephalotin-Na | 0.13 |
| Cephalexin | 1.25 |
| Cephazolin-Na | 0.25 |
| Examples | |
| 1, 4, 6, 9, 28, 31, 39, 44, 46, 50, 51, 52, 54, 56, 57, 58, 65, 69, 120, 121 | 0.0196–0.0391 |
| Examples | |
| 3, 5, 8, 14, 26, 27, 29, 32, 33, 34, 35, 38, 44, 49, 53, 55, 60, 62, 63, 64, 68, 70, 71, 73, 80, 85, 91, 92, 103, 105, 106, 108, 109, 111, 112, 113, 114, 116, 117, 118, 122, 127, 128 | 0.0625–0.078 |

As results from the values indicated in the tables, the novel acylamino-cephem-carboxylic acids are comparable with the commercial antibiotics and in numerous cases are even superior to these.

Thus, the products of the invention are valuable therapeutic agents which are suitable in outstanding manner for combatting bacterial infections. They may be used as such or together with the therapeutically usual auxiliary agents, for example tragacanth, lactose, talc, agar-agar, etc., in the form of galenic preparations, for example dragees, tablets, capsules and also in the form of solutions or suspensions, which contain the active substance in a quantity of from about 50 to 1000 mg, preferably 100 to 500 mg. For parenteral administration, suspensions or solutions in water are preferably used. However, also other physiologically tolerated organic solvents, for example ethanol, polyglycols, and solubilizers may be added. It is also possible to combine them with other active substances. Thus, it is possible to apply with the compounds of the invention, at the same time, for example other antibiotics, for example those of the series of penicillins, cephalosporins or compounds which have an influence on the symptoms of bacterial infections, for example antipyretics, analgesics and antiphlogistics.

In addition to the acylamino-cephem-carboxylic acids described in the Examples, there may also be prepared according to the invention, for example the compounds of the general formula I

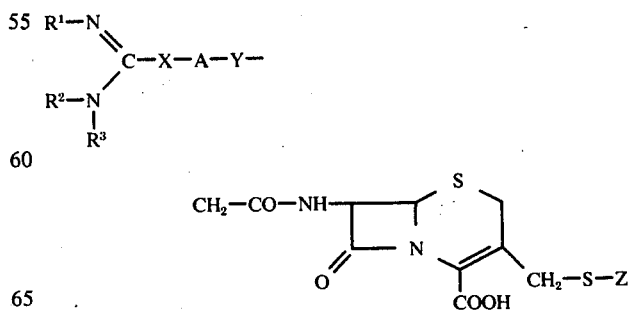

indicated in the following Table.

| R¹ | R² | R³ | X | A | Y | Z | Radical of the esterified COOH group | Salt former |
|---|---|---|---|---|---|---|---|---|
| H | H | H | — |  | — | 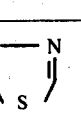 | —CH₃ | HCl |
| CH₃ | H | H | — | " | — |  | —C₂H₅ | HBr |
| CH₃ | CH₃ | H | — | " | — |  | -t-C₄H₉ | H₂SO₄ |
| H | CH₃ | CH₃ | — | " | — |  | —CH₂ | HNO₃ |
| CH₃ | CH₃ | CH₃ | — | " | — |  | —CH₂—OCH₃ | H₃C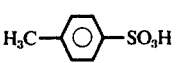SO₃H |
| C₂H₅ | H | H | — | " | — |  | —CH₂—NO₂ | H₃C—SO₃H |
| n-C₃H₇ | n-C₃H₇ | H | — | " | — |  | —n-C₁₂H₂₃ | H₂N—SO₃H |
| i-C₅H₁₁ | H | H | — | " | — |  | —CH₂—O—C(=O)—CH₃ | HCl |
| C₂H₅ | CH₃ | CH₃ | — | " | — |  | —CH₂—O—C(=O)—C(CH₃)₃ | HCl |
| —CH₂—CH₂—CH₂— | | CH₃ | — | " | — |  | 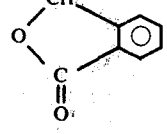 | HCl |
| CH₃—O—CH₂—CH₂ \ / CH₃—O—CH₂—CH₂ | | H | — | " | — |  | —CH₂—C(=O)— | HCl |
| H | H | H | — |  | — |  | —CH₃ | HCl |
| H | —(CH₂)₅— | | — |  | — |  | —C₂H₅ | HBr |
| —(CH₂)₂— | | H | — | " | — |  | -t-C₄H₉ | H₂SO₄ |
| H | H | H | — | " | O |  | —CH₂ | HNO₃ |
| —(CH₂)₂— | | H | — | " | O |  | —CH₂—OCH₃ | H₃C——SO₃H |

-continued

| R¹ | R² | R³ | X | A | Y | Z | Radical of the esterified COOH group | Salt former |
|---|---|---|---|---|---|---|---|---|
| | —(CH₂)₃— | H | — | " | 0 | N—N, S, phenyl | —CH₂—C₆H₄—NO₂ | H₃C—SO₃H |
| H | H | H | NH | " | — | N—N, S, cyclohexyl | -n-C₁₂H₂₃ | H₂N—SO₃H |
| | —(CH₂)₂— | H | NH | " | — | N, S (thiazole) | —CH₂—O—C(O)—CH₃ | HCl |
| | —(CH₂)₃— | H | NH | " | — | N, S, CH₃ | —CH₂—O—C(O)—C(CH₃)₃ | HBr |
| H | H | H | NH | " | 0 | N, S, phenyl | phthalide-type | HCl |
| | —(CH₂)₂— | H | NH | " | 0 | N—N, NH (triazole) | —CH₂—C(O)—C₆H₅ | HNO₃ |
| | —CH—CH₂— (CH₃) | CH₃ | — | " | — | N—N, S | —CH₃ | HCl |
| | —CH—CH₂— (n-C₄H₉) | CH₃ | — | " | — | N—N, S, CH₃ | —C₂H₅ | HBr |
| | H₃C—C(CH₂—)(CH₂—)—CH₃,H₃C | H | — | " | — | N—N, S, C₂H₅ | -t-C₄H₉ | H₂SO₄ |
| | tetrahydropyran-spiro | H | — | " | — | N—N, S, n-C₃H₇ | —CH(C₆H₅)₂ | HNO₃ |
| | cyclopentyl-CH₂ | H | — | " | — | N—N, S, n-C₄H₉ | —CH₂—C₆H₄—OCH₃ | H₃C—C₆H₄—SO₃H |
| | cyclohexylidene | H | — | " | — | N—N, S, phenyl | —CH₂—C₆H₄—NO₂ | H₃C—SO₃H |
| | bicyclic | H | — | " | — | N—N, S, piperidyl | -n-C₁₂H₂₃ | H₂N—SO₃H |
| H | H | H | — | 2,6-dimethylphenyl | — | N, S | —CH₂—O—C(O)—CH₃ | HCl |
| | —(CH₂)₄— | H | — | 4-methylphenyl | — | N, S, CH₃ | —CH₂—O—C(O)—C(CH₃)₃ | HCl |
| H | H | H | — | 2-methoxyphenyl | — | N, S, phenyl | phthalide-type | HCl |

4,016,159

17                    18

-continued

| R¹ | R² | R³ | X | A | Y Z | Radical of the esterified COOH group | Salt former |
|---|---|---|---|---|---|---|---|
| H | H | H | — | O-n-C₄H₉ (dimethylphenyl) | — N—N (triazole-NH) | —CH₂—C(=O)—C₆H₅ | HCl |
|  | —(CH₂)₃— | H | NH | " | O  N—N (thiadiazole) | —CH₃ | HCl |
| H | H | H | — | (thiophene) | — N—N—CH₃ (thiadiazole) | —C₂H₅ | HBr |
|  | —(CH₂)₂— | H | — | " | — N—N—C₂H₅ (thiadiazole) | -t-C₄H₉ | H₂SO₄ |
|  | —(CH₂)₃— | H | — | " | — N—N—n-C₃H₇ (thiadiazole) | —CH(C₆H₅)₂ | HNO₃ |
| H | H | H | — | " | O  N—N—n-C₄H₉ (thiadiazole) | —CH₂—C₆H₄—OCH₃ | H₃C—C₆H₄—SO₃H |
|  | —(CH₂)₂— | H | — | " | O  N—N—C₆H₅ (thiadiazole) | —CH₂—C₆H₄—NO₂ | H₃C—SO₃H |
|  | —(CH₂)₃— | H | — | " | O  N—N—(piperidinyl) (thiadiazole) | -n-C₁₂H₂₃ | H₂N—SO₃H |
| CH₃ | CH₃ | H | — | (phenyl) | O  N (thiazoline) | —CH₂—O—C(=O)—CH₃ | HCl |
| H | CH₃ | CH₃ | — | " | O  N—CH₃ (thiazoline) | —CH₂—O—C(=O)—C(CH₃)₃ | HCl |
| CH₃ | CH₃ | CH₃ | — | " | O  N—C₆H₅ (thiazoline) | —CH—O—C(=O)—(benzo) | HCl |
|  | CH₃—(CH₂)₅  CH₃—(CH₂)₅ (branched) | H | — | " | O  N—N (triazole-NH) | —CH₂—C(=O)—C₆H₅ | HCl |
| H | H | H | — | " | — (pyridyl-NO₂) | —CH₃ | HCl |
| CH₃ | H | H | — | " | — N—C(CH₃)₂ (thiazoline) | —C₂H₅ | HBr |
| CH₃ | CH₃ | H | — | " | — N—CH₃, N (thiazole) | -t-C₄H₉ | H₂SO₄ |
| H | CH₃ | CH₃ | — | " | — N—C₆H₅, N (thiazole) | —CH(C₆H₅)₂ | HNO₃ |

-continued

| R¹ | R² | R³ | X | A | Y | Z | Radical of the esterified COOH group | Salt former |
|---|---|---|---|---|---|---|---|---|
| CH₃ | CH₃ | CH₃ | — | " | — | 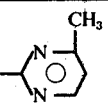 | $-CH_2-\phantom{}\bigcirc\phantom{}-OCH_3$ | $H_3C-\bigcirc-SO_3H$ |
| C₂H₅ | H | H | — | " | — | 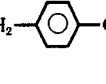 | $-CH_2-\bigcirc-NO_2$ | $H_3C-SO_3H$ |
| n-C₃H₇ | n-C₃H₇ | H | — | " | — | 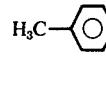 | -n-C₁₂H₂₃ | $H_2N-SO_3H$ |
| i-C₅H₁₁ | H | H | — | " | — | 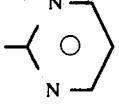 | $-CH_2-O-\underset{\underset{O}{\|\|}}{C}-CH_3$ | HCl |
| C₂H₅ | CH₃ | CH₃ | — | " | — | 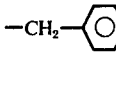 | $-CH_2-O-\underset{\underset{O}{\|\|}}{C}-C(CH_3)_3$ | HCl |
| —CH₂—CH₂—CH₂— | | CH₃ | — | " | — | 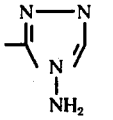 | 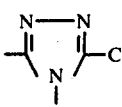 | HCl |
| CH₃—O—CH₂—CH₂⟩⟨ CH₃—O—CH₂—CH₂ | | H | — | " | — | 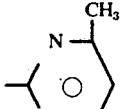 | 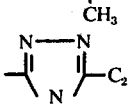 | HCl |
| H | H | H | — | " | — | 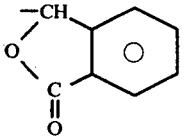 | —CH₃ | HCl |
| CH₃ | H | H | — | " | — | 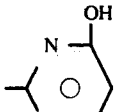 | —C₂H₅ | HBr |
| CH₃ | CH₃ | H | — | " | — | 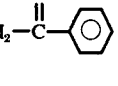 | -t-C₄H₉ | H₂SO₄ |
| H | CH₃ | CH₃ | — | " | — | 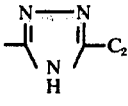 | $-CH(-\bigcirc)_2$ | HNO₃ |
| CH₃ | CH₃ | CH₃ | — | " | — | 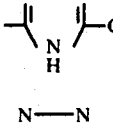 | $-CH_2-\bigcirc-OCH_3$ | $H_3C-\bigcirc-SO_3H$ |
| C₂H₅ | H | H | — | " | — | 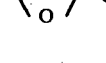 | $-CH_2-\bigcirc-NO_2$ | $H_3C-SO_3H$ |

-continued

| R¹ | R² | R³ | X | A | Y Z | | Radical of the esterified COOH group | Salt former |
|---|---|---|---|---|---|---|---|---|
| n-C₃H₇ | n-C₃H₇ | H | — | " | — | ![N-CH₂ ring with NH] | -n-C₁₂H₂₃ | HN₂—SO₃H |
| i-C₅H₁₁ | H | H | — | " | — | ![pyridyl] | —CH₂—O—C(=O)—CH₃ | HCl |
| C₂H₅ | CH₃ | CH₃ | — | " | — | ![pyridylmethyl] | —CH₂—O—C(=O)—C(CH₃)₃ | HCl |
| —CH₂—CH₂—CH₂— | | CH₃ | — | " | — | ![pyridylmethyl] | ![phthalidyl] | HCl |
| CH₃—O—CH₂—CH₂ CH₃—O—CH₂—CH₂ | | H | — | " | — | ![pyridyl N-oxide] | —CH₂—C(=O)—C₆H₅ | HCl |
| H | H | H | — | " | — | ![thiadiazine phenyl NH] | —CH₃ | HCl |
| CH₃ | H | H | — | " | — | ![triazine CH₃ OH] | —C₂H₅ | HBr |
| CH₃ | CH₃ | H | — | " | — | ![ring with NH] | -t-C₄H₉ | H₂SO₄ |
| H | CH₃ | CH₃ | — | " | — | —C(=N-NH)N=N— | —CH(C₆H₅)₂ | HNO₃ |
| CH₃ | CH₃ | CH₃ | — | " | — | —C(=N-N-CH₃)N=N— | —CH₂—C₆H₄—OCH₃ | H₃C—C₆H₄—SO₃H |
| C₂H₅ | H | H | — | " | — | —C(=N-N-C₂H₅)N=N— | —CH₂—C₆H₄—NO₂ | H₃C—SO₃H |
| n-C₃H₇ | n-C₃H₇ | H | — | " | — | —C(=N-N-n-C₃H₇)N=N— | -n-C₁₂H₂₃ | H₂N—SO₃H |
| i-C₅H₁₁ | H | H | — | " | — | ![furyl CH₃] | —CH₂—O—C(=O)—CH₃ | HCl |
| C₂H₅ | CH₃ | CH₃ | — | " | — | ![oxadiazole CH₂OH] | —CH₂—O—C(=O)—C(CH₃)₃ | HCl |

-continued

| R¹ | R² | R³ | X | A | Y | Z | Radical of the esterified COOH group | Salt former |
|---|---|---|---|---|---|---|---|---|
| —CH₂—CH₂—CH₂— | | CH₃ | — | '' | — | (4-methyl-tetrahydropyridazine-N-oxide) | (phthalidyl ester) | HCl |
| CH₃—O—CH₂—CH₂⟍⟋CH₃—O—CH₂—CH₂ | | H | — | '' | — | (benzoxazol-2-yl) | —CH₂—C(=O)—C₆H₅ | HCl |
| H | H | H | — | '' | — | (2-methyl-5-nitropyridin-yl) | — | HCl |
| CH₃ | H | H | — | '' | — | (4,5-dimethylthiazol-2-yl imino) | — | HBr |
| CH₃ | CH₃ | H | — | '' | — | (4-methyl-thiazol-2-yl, N-imino) | — | H₂SO₄ |
| H | CH₃ | CH₃ | — | '' | — | (4-phenyl-thiazol-2-yl imino) | — | HNO₃ |
| CH₃ | CH₃ | CH₃ | — | '' | — | (4-methyl-hexahydropyrimidin-2-yl) | — | H₃C—⌬—SO₃H |
| C₂H₅ | H | H | — | '' | — | (hexahydropyrimidin-2-yl) | — | H₃—SO₃H |
| n-C₃H₇ | n-C₃H₇ | H | — | '' | — | (1-amino-1,2,4-triazol-3-yl) | — | H₂N—SO₃H |
| i-C₅H₁₁ | H | H | — | '' | — | (1-amino-5-methyl-1,2,4-triazol-3-yl) | — | H₃C—SO₃H |
| C₂H₅ | CH₃ | CH₃ | — | '' | — | (4,6-dimethyl-hexahydropyrimidin-2-yl) | — | H₂N—SO₃H |
| —CH₂—CH₂—CH₂— | | CH₃ | — | '' | — | (1-amino-5-ethyl-1,2,4-triazol-3-yl) | — | HCl |

-continued

| R$^1$ | R$^2$ | R$^3$ | X | A | Y | Z | Radical of the esterified COOH group | Salt former |
|---|---|---|---|---|---|---|---|---|
| CH$_3$—O—CH$_2$—CH$_2$<br>CH$_3$—O—CH$_2$—CH$_2$ | | H | — | " | — | (N,N-heterocycle with OH) | — | HCl |
| H | H | H | — | (Cl-phenyl) | — | (imidazole-C$_2$H$_5$) | — | HCl |
| H | —(CH$_2$)$_3$— | | — | (phenyl) | — | (triazole-CH$_3$) | — | HBr |
| | —(CH$_2$)$_2$— | H | — | " | — | (oxadiazole-CH$_3$) | — | H$_2$SO$_4$ |
| H | H | H | — | " | O | (oxadiazole-phenyl) | — | HNO$_3$ |
| | —(CH$_2$)$_2$— | H | — | " | O | (oxadiazole-n-C$_4$H$_9$) | — | H$_3$C—⌬—SO$_3$H |
| | —(CH$_2$)$_3$— | H | — | " | O | (oxazoline-CH$_3$) | — | HCl |
| H | H | H | NH | " | — | (imidazoline) | — | HBr |
| | —(CH$_2$)$_2$— | H | NH | " | — | (pyridine) | — | HNO$_3$ |
| | —(CH$_2$)$_3$— | H | NH | " | — | (piperidine) | — | H$_2$SO$_4$ |
| H | H | H | NH | " | O | (pyridine N-oxide) | — | H$_2$N—SO$_3$H |
| | —(CH$_2$)$_2$— | H | NH | " | O | (piperidine N-oxide) | — | H$_3$C—⌬—SO$_3$H |
| | —CH—CH$_2$—<br>CH$_3$ | CH$_3$ | — | " | — | (thiadiazole) | — | HCl |
| | —CH—CH$_2$—<br>n-C$_4$H$_9$ | CH$_3$ | — | " | — | (thiadiazole-CH$_3$) | — | HBr |
| | H$_3$C   CH$_2$—<br>  C<br>H$_3$C   CH$_2$— | H | — | " | — | (thiadiazole-C$_2$H$_5$) | — | H$_2$SO$_4$ |

-continued

| R¹ | R² | R³ | X | A | Y | Z | Radical of the esterified COOH group | Salt former |
|---|---|---|---|---|---|---|---|---|
| | (oxane-dimethyl structure) | H | — | " | — | 5-n-C₃H₇ 1,3,4-thiadiazole | — | HNO₃ |
| | (cyclopentylmethyl) | H | — | " | — | 5-n-C₄H₉ 1,3,4-thiadiazole | — | H₃C—⟨C₆H₄⟩—CO₃H |
| | (spiro cyclohexane) | H | — | " | — | 5-phenyl 1,3,4-thiadiazole | — | H₃C—SO₃H |
| | (spiro structure) | H | — | " | — | 5-(piperidinyl) 1,3,4-thiadiazole | — | H₂N—SO₃H |
| H | H | H | — | (methylphenyl) | — | thiazole | — | HCl |
| | —(CH₂)₄— | H | — | (phenyl) | — | 4-CH₃ thiazole | — | H₃C—⟨C₆H₄⟩—SO₃H |
| H | H | H | — | (2-methoxyphenyl, OCH₃) | — | 4-phenyl thiazole | — | HCl |
| H | H | H | — | (O-n-C₄H₉ phenyl) | — | 1H-1,2,4-triazole | — | HBr |
| | —(CH₂)₃— | H | NH | (phenyl) | O | NH, phenyl-thiazine | — | HCl |
| H | H | H | — | (thienyl) | — | 5-CH₃, 6-OH pyrimidine | — | HNO₃ |
| | —(CH₂)₂— | H | — | " | — | tetrahydropyrimidine (NH) | — | H₂SO₄ |
| | —(CH₂)₃— | H | — | " | — | —C—NH / N=N / N tetrazole | — | H₃C—⟨C₆H₄⟩—SO₃H |
| H | H | H | — | " | O | —C—N—CH₃ tetrazole | — | H₂N—SO₃H |
| | —(CH₂)₂— | H | — | " | O | —C—N—C₂H₅ tetrazole | — | HCl |
| | —(CH₂)₃— | H | — | " | O | —C—N-n-C₃H₇ tetrazole | — | HBr |
| H | H | H | — | (phenyl) | — | 5-CH₃ oxazole | — | H₂SO₄ |

-continued
| R¹ | R² | R³ | X | A | Y | Z | Radical of the esterified COOH group | Salt former |
|---|---|---|---|---|---|---|---|---|
| CH₃ | H | H | — | " | — | 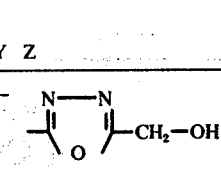 | — | HCl |
| CH₃ | CH₃ | — | " | — | — | 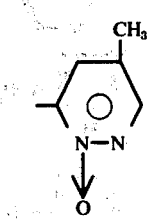 | H₂N—SO₃H | |
| H | CH₃ | CH₃ | — | " | — | 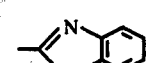 | — | 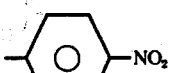 |
| | —(CH₂)₃— | H | NH | " | O |  | — | — |
| H | H | H | — | 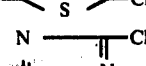 | — |  | — | — |
| | —(CH₂)₂— | H | — | " | — | 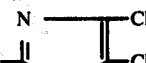 | — | — |
| | —(CH₂)₃— | H | — | " | — | 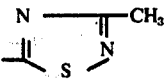 | — | — |
| H | H | H | — | " | O |  | — | — |
| | —(CH₂)₂— | H | — | " | O | 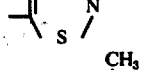 | — | — |
| | —(CH₂)₃— | H | — | " | O | 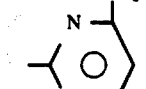 | — | — |
| CH₃ | CH₃ | CH₃ | — | 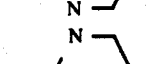 | — |  | — | — |
| C₂H₅ | H | H | — | " | — | 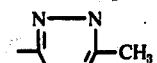 | — | — |
| n-C₃H₇ | n-C₃H₇ | H | — | " | — | 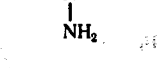 | — | — |

-continued
| R¹ | R² | R³ | X | A | Y | Z | Radical of the esterified COOH group | Salt former |
|---|---|---|---|---|---|---|---|---|
| i-C₅H₁₁ | H | H | — | " | — | 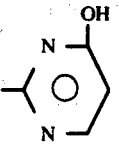 | — | — |
| | -CH-CH₂-<br>　CH₃ | CH₃ | — | " | — | 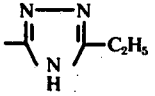 | — | — |
| | -CH-CH₂-<br>　n-C₄H₉ | CH₃ | — | " | — | 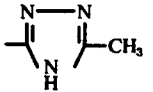 | — | — |
| 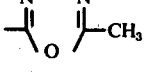 | | H | — | " | — |  | — | — |
| 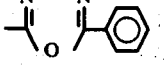 | | H | — | " | — |  | — | — |
| 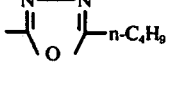 | | H | — | " | — |  | — | — |
| 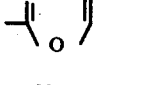 | | H | — | " | — |  | — | — |
| 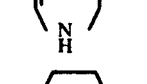 | | H | — | " | — |  | — | — |
| H | H | H | — |  | — |  | — | — |
| | -(CH₂)₄- | H | — | 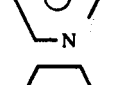 | — | 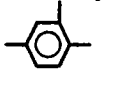 | — | — |
| H | H | H | — | 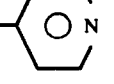 | — | 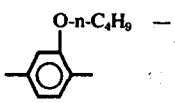 | — | — |
| H | H | H | — | 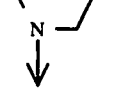 | — |  | — | — |
| H | H | H | — | 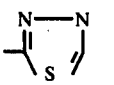 | — |  | — | — |
| H | -(CH₂)₅- | | — | 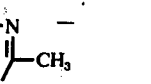 | — | | — | — |

-continued
| R¹ | R² | R³ | X | A | Y | Z | Radical of the esterified COOH group | Salt former |
|---|---|---|---|---|---|---|---|---|
|  | —(CH₂)₂— | H | — | " | — | 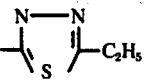 | — | — |
| H | H | H | — | " | O | 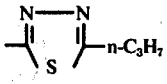 | — | — |
|  | —(CH₂)₂— | H | — | " | O | 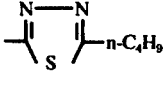 | — | — |
|  | —(CH₂)₃— | H | — | " | O | 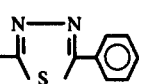 | — | — |
| H | H | H | NH | " | — | 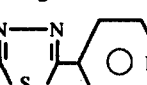 | — | — |
|  | —(CH₂)₂— | H | NH | " | — | 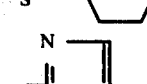 | — | — |
|  | —(CH₂)₃— | H | NH | " | — | 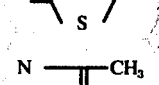 | — | — |
| H | H | H | NH | " | O | 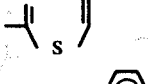 | — | — |
|  | —(CH₂)₂— | H | NH | " | O | 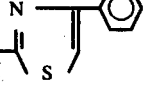 | — | — |
| H | H | H | — | " | — | 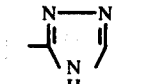 | — | — |
| CH₃ | H | H | — | " | — | 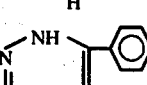 | — | — |
| CH₃ | CH₃ | H | — | " | — | 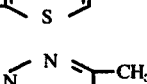 | — | — |
| H | CH₃ | CH₃ | — | " | — | 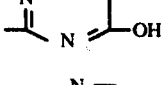 | — | — |
| CH₃ | CH₃ | CH₃ | — | " | — | 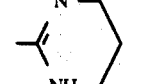 | — | — |
| C₂H₅ | H | H | — | " | — | 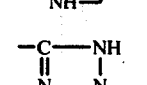 | — | — |
| n-C₃H₇ | n-C₃H₇ | H | — | " | — | 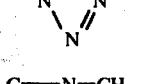 | — | — |

-continued
| R¹ | R² | R³ | X | A | Y | Z | Radical of the esterified COOH group | Salt former |
|---|---|---|---|---|---|---|---|---|
| i-C₅H₁₁ | H | H | — | " | — | 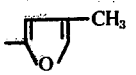 | — | — |
| C₂H₅ | CH₃ | CH₃ | — | " | — | 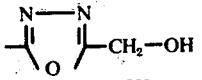 | — | — |
| —CH₂—CH₂—CH₂— | | CH₃ | — | " | — | 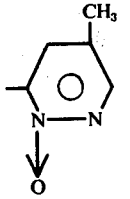 | — | — |
| CH₃—O—CH₂—CH₂<br>CH₃—O—CH₂—CH₂ | H<br>H | H | — | " | — | 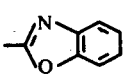 | — | — |
| H | H | H | — |  | — | 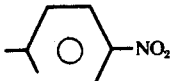 | — | — |
| H | —(CH₂)₅— | | — |  | — | 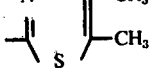 | — | — |
| | —(CH₂)₂— | | H | — | " | — | 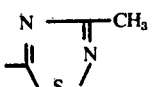 | — | — |
| H | H | H | — | " | O |  | — | — |
| | —(CH₂)₂— | | H | — | " | O | 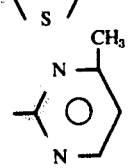 | — | — |
| | —(CH₂)₃— | | H | — | " | O | 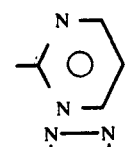 | — | — |
| H | H | H | NH | " | — |  | — | — |
| | —(CH₂)₂— | | H | NH | " | — | 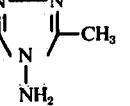 | — | — |
| | —(CH₂)₃— | | H | NH | " | — | 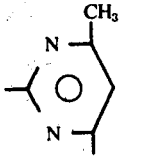 | — | — |
| H | H | H | NH | " | O | 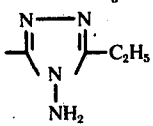 | — | — |

-continued

| R¹ | R² | R³ | X | A | Y | Z | Radical of the esterified COOH group | Salt former |
|---|---|---|---|---|---|---|---|---|
| | —(CH₂)₂— | | H | NH | '' | O | (structure) | — | — |
| H | H | H | — | (4-Cl-phenyl) | — | (triazole-C₂H₅) | — | — |
| H | | —(CH₂)₅— | | — | (phenyl) | — | (triazole-CH₃) | — | — |
| | —(CH₂)₂— | | H | — | '' | — | (oxadiazole-CH₃) | — | — |
| H | H | H | — | '' | O | (oxadiazole-phenyl) | — | — |
| | —(CH₂)₂— | | H | — | '' | O | (oxadiazole-n-C₄H₉) | — | — |
| | —(CH₂)₃— | | H | — | '' | O | (structure-CH₃) | — | — |
| H | H | H | NH | '' | — | (structure) | — | — |
| | —(CH₂)₂— | | H | NH | '' | — | (pyridine) | — | — |
| | —(CH₂)₃— | H | NH | '' | — | (pyridine) | — | — |
| H | H | H | NH | '' | O | (pyridine) | — | — |
| | —(CH₂)₂— | | H | NH | '' | O | (pyridine N-oxide) | — | — |
| H | H | H | — | (4-Cl-phenyl) | — | (thiazine-phenyl) | — | — |
| H | | —(CH₂)₅— | | — | (phenyl) | — | (structure CH₃, OH) | — | — |
| | —(CH₂)₂— | | H | — | '' | — | (structure) | — | — |
| H | H | H | — | '' | O | (tetrazole) | — | — |

-continued
| R¹ | R² | R³ | X | A | Y | Z | Radical of the esterified COOH group | Salt former |
|---|---|---|---|---|---|---|---|---|
|  | —(CH₂)₂— | H | — | " | O | 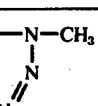 | — | — |
|  | —(CH₂)₃— | H | — | " | O | 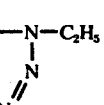 | — | — |
| H | H | H | NH | " |  | 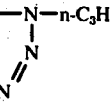 | — | — |
|  | —(CH₂)₂— | H | NH | " | — | 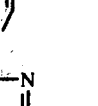 | — | — |
|  | —(CH₂)₃— | H | NH | " | — | 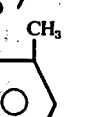 | — | — |
| H | H | H | NH | " | O | 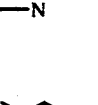 | — | — |
|  | —(CH₂)₂— | H | NH | " | O | 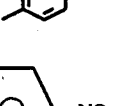 | — | — |
|  | —CH—CH₂—<br>    \|<br>    CH₃ | CH₃ | — | " | — |  | — | — |
|  | —CH—CH₂—<br>    \|<br>    n-C₄H₉ | CH₃ | — | " | — |  | — | — |
|  |  | H | — | " | — | 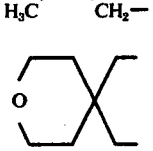 | — | — |
|  | 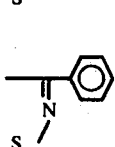 | H | — | " | — | 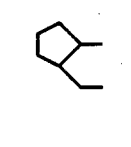 | — | — |
|  | 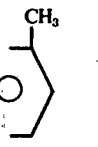 | H | — | " | — |  | — | — |
|  | 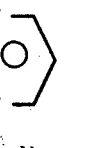 | H | — | " | — |  | — | — |
|  | 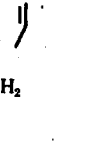 | H | — | " | — |  | — | — |

-continued
| R¹ | R² | R³ | X | A | Y | Z | Radical of the esterified COOH group | Salt former |
|---|---|---|---|---|---|---|---|---|
| H | H | H | — |  | — | 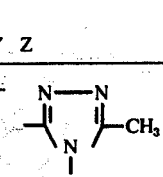 | — | — |
|  | —(CH₂)₄— | H | — |  | — | 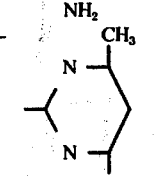 | — | — |
| H | H | H | — |  | — | 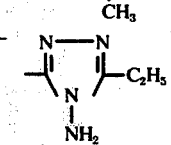 | — | — |
| H | H | H | — |  | — | 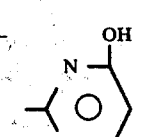 | — | — |
|  | —(CH₂)₃— | H | NH |  | O | 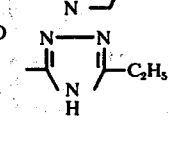 | — | — |
| H | H | H |  | — |  | — | 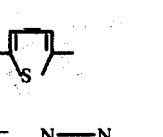 | — |
|  | —(CH₂)₂— | H | — | " | — | 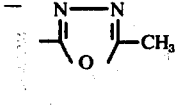 | — | — |
|  | —(CH₂)₃— | H | — | " | — | 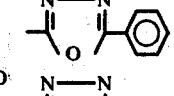 | — | — |
| H | H | H | — | " | O | 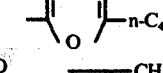 | — | — |
|  | —(CH₂)₂— | H | — | " | O | 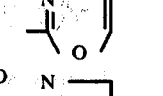 | — | — |
|  | —(CH₂)₃— | H | — | " | O | 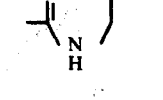 | — | — |
|  | —(CH₂)₃— | H | NH |  | O | 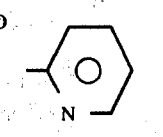 | — | — |
| H | H | H | — |  | — | 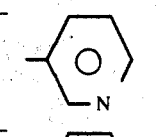 | — | — |
|  | —(CH₂)₂— | H | — | " |  | 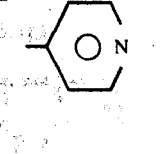 | — | — |

-continued
| R¹ | R² | R³ | X | A | Y | Z | Radical of the esterified COOH group | Salt former |
|---|---|---|---|---|---|---|---|---|
| | —(CH₂)₃— | H | — | " | — | 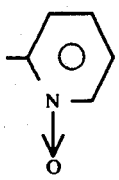 | — | — |
| | —(CH₂)₃—H | NH |  | O | — |  | — | — |
| H | H | H | — |  | — |  | — | — |
| | —(CH₂)₂— | H | — | " | — | 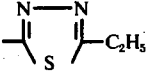 | — | — |
| | —(CH₂)₃— | H | — | " | — | 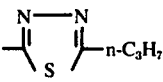 | — | — |
| H | H | H | — | " | O | 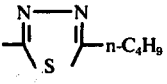 | — | — |
| | —(CH₂)₂— | H | — | " | O | 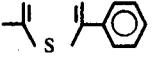 | — | — |
| | —(CH₂)₃— | H | — | " | O | 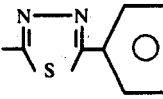 | — | — |
| | —(CH₂)₃— | H | NH |  | O |  | — | — |
| H | H | H | — |  | — | 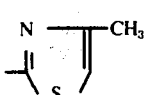 | — | — |
| | —(CH₂)₂— | H | — | " | — | 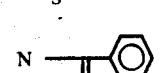 | — | — |
| | —(CH₂)₃— | H | — | " | — | 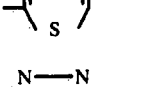 | — | — |
| | —(CH₂)₃— | H | NH |  | O | 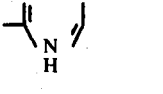 | — | — |
| H | H | H | — |  | — | 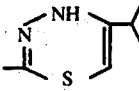 | — | — |
| | —(CH₂)₂— | H | — | " | — | 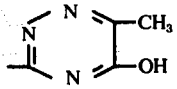 | — | — |
| | —(CH₂)₃— | H | — | " | — | 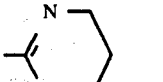 | — | — |

-continued

| R¹ | R² | R³ | X | A | Y | Z | Radical of the esterified COOH group | Salt former |
|---|---|---|---|---|---|---|---|---|
| H | H | H | — | '' | O | ![structure: C-N(CH₃) tetrazole] | — | — |
|  | —(CH₂)₂— | H | — | '' | O | ![structure: C-N(C₂H₅) tetrazole] | — | — |
|  | —(CH₂)₃— | H | — | '' | O | ![structure: C-N(n-C₃H₇) tetrazole] | — | — |
|  | —(CH₂)₃— | H | NH | ![phenylene] | O | ![structure: furan-CH₃] | — | — |
| H | H | H | — | ![thiophene] | — | ![structure: oxadiazole-CH₂—OH] | — | — |
|  | —(CH₂)₂— | H | — | '' | — | ![structure: pyridazine N-oxide with CH₂ and CH₃] | — | — |
|  | —(CH₂)₃— | H | — | '' | — | ![structure: benzoxazole] | — | — |
| H | H | H | — | ![phenylene] | — | ![structure: triazole-C₂H₅] | — | — |
| CH₃ | H | H | — | '' | — | ![structure: triazole-CH₃] | — | — |
| CH₃ | CH₃ | H | — | '' | — | ![structure: oxadiazole-CH₃] | — | — |
| H | CH₃ | CH₃ | — | '' | — | ![structure: oxadiazole-phenyl] | — | — |
| CH₃ | CH₃ | CH₃ | — | '' | — | ![structure: oxadiazole-n-C₄H₉] | — | — |
| C₂H₅ | H | H | — | '' | — | ![structure: oxazole-CH₃] | — | — |
| n-C₃H₇ | n-C₃H₇ | H | — | '' | — | ![structure: pyrazoline NH] | — | — |
| i-C₅H₁₁ | H | H | — | '' | — | ![structure: pyridine] | — | — |

-continued
| R¹ | R² | R³ | X | A | Y | Z | Radical of the esterified COOH group | Salt former |
|---|---|---|---|---|---|---|---|---|
| C₂H₅ | CH₃ | CH₃ | — | " | — | 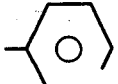 | — | — |
| —CH₂—CH₂—CH₂— | | CH₃ | — | " | — | 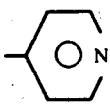 | — | — |
| CH₃—O—CH₂—CH₂\<br>CH₃—O—CH₂—CH₂ | | H | — | " | — | 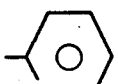 | — | — |
| H | H | H | — | " | — | 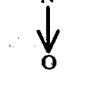 | — | — |
| CH₃ | H | H | — | " | — | 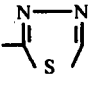 | — | — |
| CH₃ | CH₃ | H | — | " | — | 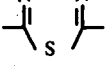 | — | — |
| H | CH₃ | CH₃ | — | " | — | 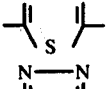 | — | — |
| CH₃ | CH₃ | CH₃ | — | " | — | 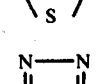 | — | — |
| C₂H₅ | H | H | — | " | — | 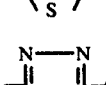 | — | — |
| n-C₃H₇ | n-C₃H₇ | H | — | " | — | 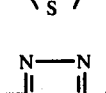 | — | — |
| i-C₅H₁₁ | H | H | — | " | — | 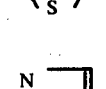 | — | — |
| C₂H₅ | CH₃ | CH₃ | — | " | — |  | — | — |
| —CH₂—CH₂—CH₂— | | CH₃ | — | " | — | 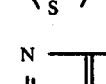 | — | — |
| CH₃—O—CH₂—CH₂\<br>CH₃—O—CH₂—CH₂ | | H | — | " | — | 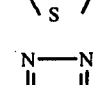 | — | — |
| —CH—CH₂—\<br>     \|\<br>   CH₃ | | CH₃ | — | " | — | 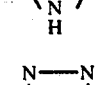 | — | — |
| —CH—CH₂—\<br>     \|\<br>  n-C₄H₉ | | CH₃ | — | " | — | 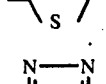 | — | — |

| R¹ | R² | R³ | X | A | Y | Z | Radical of the esterified COOH group | Salt former |
|---|---|---|---|---|---|---|---|---|
| | (H₃C)(H₃C)C(CH₂-)(CH₂-) | H | — | " | — | 5-ethyl-1,3,4-thiadiazol-2-yl | — | — |
| | tetrahydropyran-4,4-diyl-bis(CH₂) | H | — | " | — | 5-n-propyl-1,3,4-thiadiazol-2-yl | — | — |
| | cyclopentane-1,1-diyl-bis(CH₂) | H | — | " | — | 5-n-butyl-1,3,4-thiadiazol-2-yl | — | — |
| | cyclohexane-1,1-diyl-bis(CH₂) | H | — | " | — | 5-phenyl-1,3,4-thiadiazol-2-yl | — | — |
| | bicyclic-bis(CH₂) | H | — | " | — | 5-(pyridin-4-yl)-1,3,4-thiadiazol-2-yl | — | — |
| H | H | H | — | o-tolyl | — | thiazol-2-yl | — | — |
| | —(CH₂)₄— | H | — | p-tolyl | — | 4-methyl-thiazol-2-yl | — | — |
| H | H | H | — | 2-methoxyphenyl | — | 4-phenyl-thiazol-2-yl | — | — |
| H | H | H | — | 2-(n-butoxy)phenyl | — | 1H-1,2,4-triazol-3-yl | — | — |
| | —CH(CH₃)—CH₂— | CH₃ | — | phenyl | — | 6-phenyl-2H-1,3,4-thiadiazin-3-yl | — | — |
| | —CH(n-C₄H₉)—CH₂— | CH₃ | — | " | — | 5-methyl-6-hydroxy-1,2,4-triazin-3-yl | — | — |
| | (H₃C)(H₃C)C(CH₂-)(CH₂-) | H | — | " | — | 1,4,5,6-tetrahydropyrimidin-2-yl | — | — |
| | tetrahydropyran-4,4-diyl-bis(CH₂) | H | — | " | — | 1H-tetrazol-5-yl | — | — |
| | cyclopentane-1,1-diyl-bis(CH₂) | H | — | " | — | 1-methyl-tetrazol-5-yl | — | — |
| | cyclohexane-1,1-diyl-bis(CH₂) | H | — | " | — | 1-ethyl-tetrazol-5-yl | — | — |

-continued

| R¹ | R² | R³ | X | A | Y | Z | Radical of the esterified COOH group | Salt former |
|---|---|---|---|---|---|---|---|---|
| | ⋈ (spiro) | | H | — | " | — | —C(=N-N=N-)—N-n-C₃H₇ (tetrazolyl) | — | — |
| H | H | H | — | —C₆H₄— (phenylene) | — | 5-methyl-1,3,4-oxadiazol-2-yl | — | — |
| —(CH₂)₄— | | H | — | —C₆H₄— | — | 5-(hydroxymethyl)-1,3,4-oxadiazol-2-yl (—N=N—C(CH₂—OH)=... with O) | — | — |
| H | H | H | — | 4-OCH₃—C₆H₄— | — | 5-methyl-1,3,4-oxadiazin-... (N—N with CH₃, O, CH₂) with N-oxide | — | — |
| H | H | H | — | 2-O-n-C₄H₉—C₆H₄— | — | benzoxazol-2-yl | — | — |

The following Examples illustrate the invention.

EXAMPLES

The novel compounds were characterized by their spectroscopei data. They showed the absorption bands between 1755 cm⁻¹ and 1765 cm⁻¹ which are characteristic for the β-lactam ring.

EXAMPLE 1 a. 5.35 g of 4-amidinophenylacetic acid (M.p. 295° to 297° C, decomposition) were suspended in 45 ml of anhydrous benzene. Two drops of dimethylformamide and 17.9 g of thionyl chloride were added and the whole was heated for 1½ hours under reflux. After cooling, the solid product was filtered off with suction, washed with anhydrous benzene and dried under reduced pressure. 6.9 g of 4-amidino-phenylacetyl chloride-hydrochloride melting at 174° to 177° C (decomposition) were obtained.

b. 0.45 g of 4-amino-phenylacetylchloride-hydrochloride was added within about 10 minutes to a solution that had been cooled to about −2° C of 0.59 g of 3-[(1,3,4-thiadiazole-2-yl)-thiomethyl]-7-amino-Δ3-cephem-carboxylic acid and 0.45 g of sodium bicarbonate in 9ml of water and 0.9ml of acetone. A colorless crystalline precipitate formed, with foaming up, which as filtered off with suction after 1 hour at 0° C, washed with cold water, acetone and ether and dried on the air. 0.45 g of 3-[(1,3,4-thiadiazole-2-yl)-thiomethyl]-7-(4-amidino-phenylacetamido)-Δ3-cephem-4-carboxylic acid melting at about 235° C (decomposition) was obtained.

EXAMPLE 2 a. 3.00 g of 5-amidino-thienyl-2-acetic acid were suspended in 30 ml of anhydrous benzene. 1 Drop of dimethylformamide and 12 ml of thionyl chloride were added and the whole was stirred for 2 hours at room temperature. The crystalline product was filtered off with suction, washed with anhydrous benzene and dried under reduced pressure. 3.82 g of 5-amidino-thienyl-2-acetyl chloridehydrochloride were obtained.

b. In a manner analogous to that of Example 1 b, there was otained from 0.62 g of 5-amidino-thienyl-2-acetyl chloride hydrochloride and 0.81 g of 3-[(5-methyl-1,3,4-thiadiazole-2-yl)-thiomethyl]-7-amino-Δ3-cephem-4-carboxylic acid, 0.78 g of 3-[(5-methyl-1,3,4-thiadiazole-2-yl)-thiomethyl]-7-(5-amidinothienylacetamido)-Δ-3-cephem-4-carboxylic acid melting at 215° – 218° C (decomposition).

EXAMPLE 3

In a manner analogous to that of Example 1 b, there was obtained from 0.47 g of 5-amidino-thienyl-2-acetyl chloride-hydrochloride (from Example 2 a) and 0.59 g of 3-[(1,3,4-thiadiazole-2-yl)-thiomethyl]-7-amino-Δ3-cephem-4-carboxylic acid, 0.47 g of 3-[(1,3,4-thiadiazole-2-yl)-thiomethyl]-7-(5-amidinothienyl-acetamido)-Δ3-cephem-4-ccarboxylic acid melting at about 220° C (decomposition).

EXAMPLE 4

In a manner analogous to that of Example 1 b, there was obtained from 0.63 g of 4-amidino-phenyl-acetyl chloride-hydrochloride from Example 1 a and 0.82 g of 3-[(thiazole-2-yl)-thiomethyl]-7-amino-Δ3-cephem-4-carboxylic acid, 0.85 g of 3-[(thiazole-2-yl)-thiomethyl]-7-(4-amidino-phenylacetamido)-Δ3-cephem-4-carboxylic acid melting at 242° to 244° C (decomposition).

EXAMPLE 5

In a manner analogous to that of Example 1 b, there was obtained from 0.47 g of 4-amidino-phenyl-acetyl chloride-hydrochloride (from Example 1 a) and 0.62 g of 3-[(4-methylthiazole-2-yl)-thiomethyl]-7-amino-Δ3-cephem-4-carboxylic acid, 0.59 g of 3-[(4-methyl-thioazole-2-yl)-thiomethyl]-7-(4-amidinophenyl-acetamido)-Δ3-cephem-4-carboxylic acid melting at 244° – 246° C (decomposition).

EXAMPLE 6 a. 21 g of 4-guanidino-phenylacetic acid were added to 200 ml of thionyl chloride that had been cooled to 0° C. After 15 minutes at 0° C, the whole was stirred for 15 minutes at room temperature, the product as precipitated with 500 ml of anhydrous ether, filtered off with suction, washed with anhydrous ether and dried under reduced pressure. 24.7 g of 4-guanidino-phenylacetyl chloride hydrochloride melting at 127° to 130° C were obtained.

b. In a manner analogous to that of Example 1 b, there was obtained from 9.75 g of 4-guanidino-phenylacetyl chloride-hydrochloride and 0.90 g of 3-[(5-methyl-1,3,4-thiadiazole-2-yl)-thiomethyl]-7-amino-Δ3-cephem-4-carboxylic acid, 1.01 g of 3-[(5-methyl-1,3,4-thiadiazole-2-yl)-thiomethyl]-7-(4-guanidino-phenylacetamido)-Δ3-cephem-4-carboxylic acid melting from 220° C onwards (decomposition).

EXAMPLE 7

In a manner analogous to that of Example 1 b, there was obtained from 0.60 g of 4-guanidino-phenylacetyl chloride-hydrochloride (from Example 6 a) and 0.69 g of 3-[(4-methyl-tiazole-2-yl)-thiomethyl]-7-amino-Δ3-cephem-4-carboxylic acid, 0.92 g of 3-[(4-methyl-thiomethyl]-7-(4-guanidino-phenylacetamido)-Δ3-cephem-4-carboxlic acid melting from 215° C onwards (decomposition).

EXAMPLE 8

In a manner analogous to that of Example 1 b, there was obtained from 0.62 g of 4-guanidino-phenylacetyl chloride-hydrochloride (from Example 6 a) and 3-[(thiazole-2-yl)-thiomethyl]-7-amino-Δ3-cephem-4-carboxylic acid, 0.74 g of 3-[(thiazole-2-yl)-thiomethyl]-7-(4-guanidino-phenylacetamido-Δ3-cephem-4-carboxylic acid melting from 225° C onwards (decomposition).

EXAMPLE 9

In a manner analogous to that of Example 1 b, there was obtained from 0.82 g of 4-guanidino-phenylacetyl chloride-hydrochloride (from Example 6 a) and 3-[(1,3,4-thiadiazole-2-yl)-thiomethyl]-7-amino-Δ3-cephem-4-carboxylic acid, 1.39 g of 3-[(1,3,4-thiadiazole-2-yl)-thiomethyl]-7-(4-guanidino-phenylacetamido)-Δ3-cephem-4-carboxylic acid melting at about 235° C (decomposition).

EXAMPLE 10 a. 10 g of 4-(2-imidazolinyl)-phenylacetic acid (melting point 196° to 197° C) were stirred with 150 ml of anhydrous benzene and 90 ml of thionyl chloride for 5 hours at 50° to 60° C. After cooling, the crystalline product was filtered off with suction, washed with anhydrous benzene and dried under reduced pressure. 11 g of 4-(2-imidazolinyl)-phenyl-acetyl chloride-hydrochloride were obtained.

b. In a manner analogous to that of Example 1 b, there was obtained from 0.57 g of 4-(2-imidazolinyl)-phenylacetyl chloride-hydrochloride and 0.69 g of 3-[(4-methyl-thiazole-2-yl)-thiomethyl]-7-amino-Δ3-cephem-4-carboxylic acid, 0.48 g of 3-[(4-methyl-thiazole-2-yl)-thiomethyl]-7-[4-(imidazoline-2-yl)-phenylacetamido]-Δ3-cephem-4-carboxylic acid melting at 175° to 177° C (decomposition).

EXAMPLE 11 a. 30.0 g of 4-(1,4,5,6-tetrahydro-pyrimide-2-yl)-phenylacetic acid hydrochloride (melting point 256° to 258° C) were stirred for 6 hours at 55° C with 350 ml of anhydrous benzene, 270 ml of pure thionyl chloride and 5 drops of dimethylformamide. After cooling, the crystalline product was filtered off with suction, washed with anhydrous benzene and dried under reduced pressure. 31.4 g of 4-(1,4,5,6-tetrahydro-pyrimide-2-yl)-phenylacetyl chloride-hydrochloride were obtained.

b. In a manner analogous to that of Example 1 b, there were obtained from 2.40 g of 4-(1,4,5,6-tetrahydro-pyrimide-2-yl)-phenylacetyl chloride and 2.48 g of 3-[(5-methyl-1,3,4-thiadiazole-2-yl)-thiomethyl]-7-amino-Δ3-cephem-4-carboxylic acid, 2.14 g of 3-[(5-methyl-1,3,4-thiadiazole-2-yl)-thiomethyl]-7-[4-(1,4,5,6-tetrahydro-pyrimide-2-yl)-phenylacetamido]-Δ3-cephem-4-carboxylic acid melting at about 195° C (decomposition).

EXAMPLE 12

In a manner analogous to that of Example 1 b, there was obtained from 0.85 g of 4-(2-imidazolinyl)-phenylacetyl chloride-hydorchloride (from Example 10 a) and 1.04 g of 3-[(5-methyl-1,3,4-thiadiazole-2-yl)-thiomethyl]-7-amino-Δ3-cephem-4-carboxylic acid, 1.45 g of 3-[(5-methyl-1,3,4-thiadiazole-2-yl)-thiomethyl]-7-[4-(imidazoline-2-yl)-phenylacetamido]-Δ3-cephem-4-carboxylic acid melting at about 170° to 174° C (decomposition).

EXAMPLE 13

1.18 g of 7-[4-(1,4,5,6-tetrahydro-pyrimide-2-yl)-phenylacetamido]-cephalosporanoic acid were dissolved in 25 ml of water and 2.5 ml of acetone, 0.53 g of 3-phenyl-5-mercapto-1,2,4-thiadiazole were added and the reaction mixture was stirred for 2 hours at 70° to 80° C under nitrogen. During the total reaction time the pH-value was kept at 6.2 by the addition of an aqueous sodium bicarbonate solution. The product crystallized slowly from the clear solution. It was cooled, filtered off with suction, washed with water and dried under reduced pressure over $P_2O_5$. There was obtained 1.2 g of 3-[(3-phenyl-1,2,4-thiadiazol-2-yl)-thiomethyl]-7-[4-(1,4,5,6-tetrahydro-pyrimide-2-yl)-phenyl-acetamido]-Δ3-cephem-4-carboxylic acid melting at about 216° C (decomposition).

EXAMPLE 14

3.00 g. of 4-(1,4,5,6-tetrahydropyrimide-2-yl)-phenylacetyl chloride-hydrochloride (from Example 11 a) were added within about 10 minutes to a solution that had been cooled to 0° C of 2.72 g of 7-amino-cephalosporanoic acid (7-ACS) and 2.52 g of sodium bicarbonate in 50 ml of water and 5 ml of acetone. With foaming up, a clear solution formed. After 1 hour at 0° C, the pH-value was adjusted to 3.8 by means of dilute hydrochloric acid, the unreacted 7-ACS was filtered off, the filtrate was combined with 2.12 g of 2-mercapto-4-phenyl-thiazole and the reaction mixture was stirred for 2 hours at 70° to 80° C under nitrogen. The pH-value was controlled during the total reaction time and maintained constant at 6.0 to 6.2 by dropwise adding aqueous sodium carbonate solution, whereupon the product precipitated. After cooling, the product was filtered off with suction and boiled with acetone. 1.53 g of 3-[(4-phenyl-thiazole-2-yl)-thiomethyl]-7-[4-(1,4,5,6-tetrahydropyrimide-2-yl)-phenylacetamido]-Δ3-cephem-4-carboxylic acid melting at about 235° C (decomposition were obtained.

EXAMPLE 15

The process described in Example 14 was repeated with the difference that 1.45 g of 2-mercapto-4-methyl-thiazole were used instead of 2-mercapto-4-phenyl-thiazole. After cooling, the almost clear solution was filtered, the solvent was removed by distillation, the residue was dissolved in methanol, filtered and the product was precipitated with ether. 2.75 g of 3-[(4-methyl-thiazole-2-yl)-thiomethyl]-7-[4-(1,4,5,6-tetrahydropyrimide-2-yl)-phenylacetamido]-Δ3-cephem-4-carboxylic acid melting at about 195° C (decomposition) were obtained.

EXAMPLE 16

In a manner analogous to that of Example 1 b, 1.23 g of 4-(1,4,5,6-tetrahydropyrimide-2-yl)-phenylacetyl chloride-hydrochloride were reacted with 1.40 g of 3-[(4-methyl-thiazole-2-yl)-thiomethyl]-7-amino-Δ3-cephem-4-carboxylic acid, whereupon a clear solution formed, with foaming up. The pH-value was adjusted to 3.8 by means of dilute hydrochloric acid, unreacted aminocephem-carboxylic acid was filtered off, the solvent was removed by distillation from the filtrate, the residue was dissolved in warm methanol, the solution was filtered and the product was precipitated with ether. 1.4 g of 3-[(4-methyl-thiazole-2-yl)-thiomethyl]-7-[4-(1,4,5,6-tetrahydro-2-yl)-phenylacetamido]-Δ3-cephem-4-carboxylic acid was obtained, which compound was identical with the product obtained according to Example 15.

EXAMPLE 17

The process described in Example 15 was repeated with the difference that 1.26 g of 3-mercapto-5-methyl-2,3,4-triazole were used instead of 2-mercapto-4-methyl-thiazole. 3.0 g of 3-[(methyl-1,2,4,-triazole-3-yl)-thiomethyl]-7-[4-(1,4,5,6-tetrahydropyrimide-2-yl)-phenylacetamido]-Δ3-cephem-4-carboxylic acid melting at about 215° C (decomposition) were obtained.

EXAMPLE 18

The process described in Example 15 was repeated with the difference that 1.98 g of 2-mercapto-5-methyl-1,3,4-thiadiazole dissolved in 20 ml of acetone were used instead of 2-mercapto-4-methyl-thiazole. 4.8 g of 3-[(5-methyl-1,3,4-thiadiazole-2-yl)-thiomethyl]-7-[4-(1,4,5,6-tetrahydropyrimide-2-yl)-phenylacetamido[-Δ3-cephem-4-carboxylic acid were obtained, which compound was identical with the product obtained according to Example 11.

EXAMPLE 19

The process described in Example 15 was repeated with the difference that 0.89 g of 2-mercapto-1,3,4-thiadiazole was used instead of 2-mercapto-4-methyl-thiazole. After removal of the solvent by distillation, the residue was dissolved in dimethylsulfoxide, the solution was filtered and the product was precipitated with acetone. 2.75 g of 3-[(1,3,4-thiadiazole-2-yl)-thiomethyl]-7-[4-(1,4,5,6-tetrahydropyrimide-2-yl)-phenylacetamido]-Δ3-cephem-4-carboxylic acid melting from about 160° C onwards (decomposition) were obtained.

EXAMPLE 20

The process described in Example 13 was repeated with the difference that 0.32 g of 2-mercapto-thiazole was used instead of the 3-phenyl-5-mercapto-1,2,4-thiadiazole. After cooling, the clear solution was lyophilized, the residue was dissolved in dimethyl-sulfoxide, filtered and the product was precipitated from the filtrate with the aid of acetone and ether. 0.90 g of 3-[(thiazole-2-yl)-thiomethyl]-7-[4-(1,4,5,6-tetrahydropyrimide-2-yl)-phenylacetamido]-Δ3-cephem-4-carboxylic acid melting at about 215° C (decomposition) was obtained.

EXAMPLE 21

The process described in Example 20 was repeated with the difference that 0.39 g of 2-mercapto-5-methyl-6-hydroxy-1,3,4-triazine was used instead of the 2-mercapto-thiazole. 1.3 g of 3-[(5-methyl-6-hydroxy-1,3,4-triazine-2-yl)-thiomethyl]-7-[4-(1,4,5,6-tetrahydropyrimide-2-yl)-phenylacetamido]-Δ3-cephem-4-carboxylic acid melting at about 220° C (decomposition) were obtained.

EXAMPLE 22

The process described in Example 11 b was repeated with the difference that, after 1 hour at 0° C, the product was precipitated as hydrochloride with 6N-HCl. After suction-filtration and washing with cold water, acetone and ether, 2.5 g of 3-[(5-methyl-1,3,4-thiadiazole-2-yl)-thiomethyl]-7-[4-(1,4,5,6-tetrahydropyrimide-2-yl)-phenylacetamido]-Δ3-cephem-4-carboxylic acid hydrochloride were obtained in the form of slightly yellowish crystals melting at about 175° C (decomposition) were obtained.

EXAMPLE 23

0.62 g of 4-amidino-phenylacetyl chloride-hydrochloride (from Example 1 a was added, within about 10 minutes to a solution, that had been cooled to about 0° C, of 0.78 g of 3-[(5-methyl-1,3,4-triazole-3-yl)-thiomethyl]-7-amino-Δ 3-cephem-4-carboxylic acid and 0.60 g of sodium bicarbonate in 25 ml of water and 2.5 ml of acetone. An almost clear solution formed, with foaming up. After 1 hour at 0° C, the solution was filtered, the filtrate was acidified to pH 3.8 by means of dilute hydrochloric acid, unreacted amino-cephem-carboxylic acid was filtered off, the filtrate was lyophilized, the residue was dissolved in warm methanol, filtered and the product was precipitated from the filtrate by means of ether. 0.65 g of 3-[(5-methyl-1,2,4-triazole-3-yl)-thiomethyl]-7-(4-amidino-phenylacetamido)-Δ3-cephem-4-carboxylic acid melting at about 215° C (decomposition) was obtained.

EXAMPLE 24

In a manner analogous to that of Example 23, there was obtained from 0.75 g of 4-amidino-phenylacetyl chloride-hydrochloride and 0.91 g of 3-[(2,3,4-triazol-3-yl)-thiomethyl]-7-amino-Δ3-cephem-4-carboxylic acid, 0.80 g of of 3-[(1,2,4-triazole-3-yl)-thiomethyl]-

7-(4-amidino-phenylacetamido)-Δ3-cephem-4-carboxylic acid melting at above 300° C (decomposition).

EXAMPLE 25

In a manner analogous to that of Example 23, there was obtained from 0.90 g of 4-(1,4,5,6-tetrahydropyrimide-2-yl)-phenylacetyl chloride-hydrochloride (from Example 11 a) and 0.99 g of 3-[(1,3,4-thiadiazole-2-yl)-thiomethyl]-7-amino-Δ3-cephem-4-carboxylic acid, 0.95 g of 3-[(1,3,4-thiadiazole-2-yl)-thiomethyl]-7-[4-(1,4,5,6-tetrahydropyrimide-2-yl)-phenylacetamido]Δ3-cephem-4-carboxylic acid, which compound was found to be identical with the product of Example 19.

EXAMPLE 26

In a manner analogous to that of Example 1 b there was obtained from 0.90 g of 4-(1,4,5,6-tetrahydropyrimide-2-yl)-phenylacetyl chloride-hydrochloride (from Example 11 a) and 0.99 g of 3-[(1,3,4-thiadiazole-2-yl)-thiomethyl]-7-amino-Δ3-cephem-4-carboxylic acid, 0.95 g of 3-[(1,3,4-thiadiazole-2-yl)-thiomethyl]-7-[4-(1,4,5,6-tetrahydropyrimide-2-yl)-phenylacetamido]-Δ3-cephem-4-carboxylic acid, which compound was found to be identical with the product of Example 19.

EXAMPLE 26

In a manner analogous to that of Example 1 b, there was obtained from 0.24 g of 3-[(5-methyl-1,3,4-thiazole-2-yl)-thiomethyl]-7-amino-Δ3-cephem-4-carboxylic acid and 0.18 g of 4-amidinophenylacetyl chloride-hydrochloride (Example 1 a), 0.28 g of 3-[(5-methyl-1,3,4-thiadiazole-2-yl)-thiomethyl]-7-(4-amidinophenylacetamido)-Δ3-cephem-4-carboxylic acid melting at 220° to 222° C (decomposition).

EXAMPLE 27 a. 9.7 g of 4-amidinophenoxyacetic acid (M.p. 324° to 326° C) were suspended in 50 ml of anhydrous benzene, 29.7 of thionyl chloride were added and the whole was heated for 1 hour on the steam bath under reflux. After the reaction mixture had cooled, the solid product was filtered off with suction. 11.4 g of 4-amidinophenoxyacetyl chloride-hydrochloride melting at 142° – 143° C (with decomposition) were obtained.

b. A solution of 0.61 g of 3-[(4-phenyl-1,3-thiazole-2-yl)-thiomethyl]-7-amino-Δ3-cephem-4-carboxylic acid and 0.50 g of sodium carbonate in 10 ml of water and 2 ml of acetone was combined protionwise at −5° C with a suspension of 0.50 g of 4-amidinophenoxyacetyl chloride-hydrochloride in 5 ml of acetone. After 2 hours at 0° C, the precipitate was filtered off with suction, washed with acetone and ether and dried under reduced pressure. 0.48 g of 3-[(4-phenyl-1,3-thiazole-2-yl)-thiomethyl]-7-(4-amidinophenoxy-acetamido)-Δ3-cephem-4-carboxylic acid melting at 235° to 240° C (with decomposition) was obtained.

EXAMPLE 28

In a manner analogous to that of Example 1 b, there was obtained from 0.78 g of 3-[(5-phenyl-1,3,4-oxadiazole-2-yl)-thiomethyl]-7-amino-Δ3-cephem-4-carboxylic acid and 0.50 g of 4-amidinophenoxyacetyl chloride-hydrochloride (from Example 27 a), 0.65 g of 3-[(5-5-phenyl-1,3,4-oxadiazole-2-yl)-thiomethyl]-7-(4-amidino-phenoxyacetamido)-Δ3-cephem-4-carboxylic acid melting at 230° to 235° C was obtained.

EXAMPLE 29

In a manner analogous to that of Example 1 b, there was obtained from 1.28 g of 3-[(pyride-2-yl)-thiomethyl]-7-amino-Δ3-cephem-4-carboxylic acid and 0.99 g of 4-amidino-phenoxyacetyl chloride-hydrochloride (from Example 27 a), 1.2 g of 3-[(pyride-2-yl)-thiomethyl]-7-(4-amidinophenoxyacetamido)-Δ3-cephem-4-carboxylic acid melting at 270° to 274° C (decomposition).

EXAMPLE 30

In a manner analogous to that of Example 1 b, there was obtained from 1.00 g of 3-[(Δ2-thiazolidine-2-yl)-thiomethyl]-7-amino-Δ3-cephem-4-carboxylic acid and 0.75 g of 4-amidinophenoxyacetyl chloride-hydrochloride (from Example 27 a), 0.80 g of 3-[(Δ2-thiazolidine-2-yl)-thiomethyl]-7-(4-amidinophenoxyacetamido)-Δ3-cephem-4-carboxylic acid melting at 250° to 255° C (with decomposition).

EXAMPLE 31

In a manner analogous to that of Example 1 b, there was obtained from 0.80 g of 3-[(1-phenyl-1-H-tetrazole-5-yl)-thiomethyl]-7-amino-Δ3-cephem-4-carboxylic acid and 0.50 g of 4-aminophenoxyacetyl chloride-hydrochloride, 0.85 g of 3-[(1-phenyl-1-H-tetrazole-5yl)-thiomethyl]-7-(4-amidinophenoxyacetamido)-Δ3-cephem-4-carboxylic acid melting at 220° to 225° C (decomposition).

EXAMPLE 32 a. 5.56 g of 4-N-n-hexylamidino)-phenoxyacetic acid [melting point 156° C (decomposition)] were suspended in 25 ml of anhydrous benzene, 10 ml of thionyl chloride and 0.2 ml of dimethylformamide were added and the whole was stirred for 3 hours at 55° to 60° C. After cooling of the reaction mixture, the precipitate was filtered off with suction, washed with ether and dried under reduced pressure. 5.14 g of 4-(N-n-hexylamidino)phenoxyacetyl chloride-hydrochloride melting at 164° to 165° C were obtained.

b. A suspension of 1.0 g of 4-(N-n-hexylamidino)-phenoxyacetyl chloride-hydrochloride was introduced portionwise into the solution of 0.98 g of 3-[(5-methyl-1,3,4-oxadiazole-2-yl)-thiomethyl]-7-amino-Δ3-cephem-4-carboxylic acid and 0.75 g of sodium bicarbonate in 7.5 ml of water and 1.5 ml of acetone at −5° C. The whole was stirred for 1 hour at −5° C, the solution was subsequently adjusted to pH 4 and allowed to stand overnight at 0° C. after filtration, the solution was concentrated to dryness, the residue was triturated with absolute ethanol and the ethanolic filtrate was concentrated to dryness. Upon trituration of the residue obtained with ether, 0.75 g of 3-[(5-methyl-1,3,4-oxadiazole-2-yl)-thiomethyl]-7-[4-(N-n-hexylamidino)-phenoxyacetamido]-Δ3-cephem-4-carboxylic acid melting at 150° to 155° C (decomposition) was obtained.

EXAMPLE 33

In a manner analogous to that of Example 32 b, there was obtained from 0.69 g of 3-[(5-methyl-1,3,4-thiadiazole-2-yl)-thiomethyl]-7-amino-Δ3-cephem-4-carboxylic acid and 0.67 g of 4-(N-n-hexylamidino)-phenoxyacetyl chloride-hydrochloride (from Example 32 a), 0.56 g of 3-[(5-methyl-1,3,4-thiadiazole-2-yl)-thiomethyl]-7-[4-(N-n-hexylamidion)-phenoxyacetamido]-Δ3-cephem-4-carboxylic acid melting at 165° to 167° C (decomposition).

EXAMPLE 34

1.45 g of 4-(1,4,5,6-tetrahydropyrimide-2-yl)-phenoxyacetyl chloride-hydrochloride was added portionwise, at −5° C, to the solution of 1.72 g of 3-[(5-methyl-1,3,4-thiadiazole-2-yl)-thiomethyl]-7-amino-Δ3-cephem-4-carboxylic acid and 1.15 g of sodium bicarbonate in 25 ml of water and 2.5 ml of acetone. After having stirred for 1 hour, the mixture was adjusted to pH 4, filtered and the filtrate was evaporated to dryness. The residue was dissolved in 20 ml of dimethyl-sulfoxide, the whole was filtered and the filtrate was added dropwise, while cooling with ice, into 250 ml of acetone. The precipitate was filtered off with suction, washed with acetone and dried under reduced pressure. 1.78 g of 3-[(5-methyl-1,3,4-thiadizole-2-yl)-thiomethyl]-7-[4-(1,4,5,6-tetrahydropyromide-2-yl)-phenoxyacetamido]-Δ3-cephem-4-carboxylic acid melting at 190° to 195° C (decomposition) were obtained.

EXAMPLE 35

A solution of 1.03 g of 3-[(5-methyl-1,3,4-thiadiazole-2-yl)-thiomethyl]-7-amino-Δ3-cephem-4-carboxylic acid and 0.85 g of sodium bicarbonate in 25 ml of water and 2.5 ml of acetone. was combined at −5° C portionwise with a suspension of 0.75 g of 4-amidino-phenoxyacetyl chloride-hydrochloride (from Example 27 a) in 10 ml of acetone. The whole was stirred for 1 hour at 0° C, the almost clear solution was filtered and acidified to pH 1 by means of 6N-hydrochloric acid. The mixture was allowed to stand for some time at 0° C, the precipitate was filtered off with suction, washed with water and dried under reduced pressure. 1.2 g of 3-[(5-methyl-1,3,4-thiadiazole-2-yl)-thiomethyl]-7-[4-amidinophenoxy-acetamido]-Δ3-cephem-4-carboxylic acid hydrochloride melting at 165° to 167° C (decomposition) was obtained.

EXAMPLE 36 a. A suspension of 4.4 g of 4-(2-imidazolinyl)-phenoxyacetic acid (melting point 278°–280° C (decomposition)) in 25 ml of anhydrous benzene was combined with 25 ml of thionyl chloride and the whole was heated for 3 hours under reflux. After cooling of the reaction mixture, the solid product was filtered off with suction and dried under reduced pressure. 4.9 g of 4-(2-imidazolinly)-phenoxyacetyl chloride-hydrochloride melting from 195° C onwards were obtained.

b. 0.83 g of 4-(2-imidazolinyl)-phenoxyacetyl chloride-hydrochloride was added within some minutes to a solution that had been cooled to about −5° C of 1.03 g of 3-[(5-methyl-1,3,4-thiadiazole-2-yl)-thiomethyl]-7-amino-Δ3-cephem-4-carboxylic acid and 0.75 g of sodium bicarbonate in 10 ml of water and 2 ml of acetone. After 1 hour at 0° C, the solution was filtered, adjusted to pH 4 and allowed to stand overnight at 0° C. The precipitate that had separated was filtered off with suction and after washing with water and acetone and drying under reduced pressure, 0.77 g of 3-[(5-methyl-1,3,4-thiadiazole-2-yl)-thiomethyl]-7-[4-(imidazoline-2-yl)-phenoxyacetamido]-Δ3-cephem-4-carboxylic acid melting at 175° to 182° C (decomposition) was obtained.

EXAMPLE 37

In a manner analogous to that of Example 36 b, there were obtained from 1.86 g of 4-(2-imidazolinyl)-phenoxyacetyl chloride-hydrochloride (Example 36 a) and 2.3 g of 3-[(5-n-propyl-1,3,4-thiadiazole-2-yl)-thiomethyl]-7-amino-Δ3-cephem-4-carboxylic acid, 2.0 g of 3-[(5 -n-propyl-1,3,4-thiadiazole-2-yl)-thiomethyl]-7-[4-(imidazoline-2-yl)-phenoxyacetamido]-Δ3-cephem-4-carboxylic acid melting at 165° to 168° C (decomposition).

EXAMPLE 38

In a manner analogous to that of Example 36 b, there was obtained from 0.65 g of 3-[(5-methyl-1,3,4-oxadiazole-2-yl)-thiomethyl]-7-amino-Δ3-cephem-4-carboxylic acid and 0.50 g of 4-amidinophenoxyacetyl chloride-hydrochloride (Example 27 a), 0.68 g of 3-[(5-methyl-1,3,4-oxadiazole-2-yl)-thiomethyl]-7-(4-amidinophenoxy-acetamido)-Δ3-cephem-4-carboxylic acid melting at 240° to 245° C (decomposition).

EXAMPLE 39

In a manner analogous to that of Example 36 b, there was obtained from 0.78 g of 3-[(5-phenyl-1,3,4-oxadiazole-2-yl)-thiomethyl]-7-amino-Δ3-cephem-4-carboxylic acid and 0.67 g of 4-(N-n-hexylamidino-phenoxyacetyl chloride-hydrochloride (from Example 32 a), 0.62 g of 3-[(5-phenyl-1,3,4-oxadiazole-2-yl)-thiomethyl]-7-/4-(N-n-hexylamidino)-phenoxyacetamido]-Δ3-cephem-4-carboxylic acid melting at 160° C (decomposition).

EXAMPLE 40

In a manner analogous to that of Example 36 b, there were reacted 1.8 g of 3-[(5-n-propyl-1,3,4-oxadiazole-2-yl)-thiomethyl]-7-amino-Δ3-cephem-4-carboxylic acid and 1.25 g of 4-amidino-phenoxyacetyl chloride-hydrochloride (from Example 36 b). After dissolution and re-precipitation of the crude product (1.5 g) from a mixture of dimethyl-sulfoxide and acetone 0.78 g of 3-[(5-n-propyl-1,3,4-oxadiazole-2-yl)-thiomethyl]-7-(4-amidinophenoxyacetamido)-Δ3-cephem-4-carboxylic acid melting at 230° to 240° C (decomposition) were obtained.

EXAMPLE 41

In a manner analogous to that of Example 36 b, there was obtained from 1.0 g of 3-[(5-n-propyl-1,3,4-oxadiazole-2-yl)-thiomethyl]-7-amino-Δ3-cephem-4-carboxlic acid and 0.83 g of 4-(2-imidazolinyl)-phenoxyacetyl chloride-hydrochloride (from Example 36 a), 0.47 g of 3-[(5-n-propyl-1,3,4-oxadiazole-2-yl)-thiomethyl]-7-[4-(imidazoline-2-yl)-phenoxyacetamido]-Δ3-cephem-4-carboxylic acid melting at 178° to 182° C (decomposition).

EXAMPLE 42

In a manner analogous to that of Example 36 b, there was obtained from 0.87 g of 3-[(1-methyl-1-H-tetrazole-5-yl)-thiomethyl]-7-amino-Δ3-cephem-4-carboxylic acid and 0.63 g of 4-amidino-phenoxyacetyl chloride-hydrochloride (example 27 a), 0.84 g of 3-[(1-methyl-1-H-tetrazole-5-yl)-thiomethyl]-7-(4-amidinophenoxy-acetamido)-Δ3-cephem-4-carboxylic acid melting at 250° to 225° C (decomposition).

EXAMPLE 43

In a manner analogous to that of Example 36 b, there was obtained from 0.53 g of 3-[(1-methyl-1H-tetrazole-5-yl)-thiomethyl]-7-amino-Δ3-cephem-4-carboxylic acid and 0.40 g of 4-(2-imidazolinyl)-phenylacetyl chloride-hydrochloride (from Example 10 a), 0.60 g of 3-[(1-methyl-1-H-tetrazole-5-yl)-thiomethyl]-7-[4-(2-imidazolinyl)-phenylacetamido]-Δ3-cephem-4-carboxylic acid melting at 255° to 260° C (decomposition).

EXAMPLE 44

A mixture of 1.3 g of 7-(4-amidino-phenylacetamido)-cephalosporanoic acid in 40 ml of water and 10 ml of acetone was combined under nitrogen with 0.31 g of sodium bicarbonate and 0.58 g of 2-n-propyl-5-mercapto-1,3,4-oxadiazole and heated for 5 hours to 70° C. After cooling to 0° C, the precipitate was filtered off with suction and washed with water and acetone. After drying under reduced pressure, there were obtained 1.15 g of 3-[(5-n-propyl-1,3,4-oxadiazole-2-yl)-thiomethyl]-7-(4-amidino-phenylacetamido)-Δ3-cephem-4-carboxylic acid melting at 248° to 253° C (decomposition).

EXAMPLE 45

In a manner analogous to that of Example 44, there was obtained from 1.3 g of 7-(4-amidino-phenylacetamido)-cephalosporanoic acid and 0.53 g of 2-methyl-5-mercapto-1,3,4-thiadiazole, 1.15 g of 3-[(5-methyl-1,3,4-thiadiazole-2-yl)-thiomethyl]-7-(4-amidinophenylacetamido)-Δ3-cephem-4-carboxylic acid melting at 220° to 222° C (decomposition).

EXAMPLE 46

A mixture of 0.90 g of 7-(4-amidino-phenoxyacetamido)-cephalosporanoic acid in 10 ml of water and 1 ml of acetone was adjusted to pH 7 by means of sodium bicarbonate. After addition of 0.17 g of sodium bicarbonate and 0.29 g of 2-methyl-5-mercapto-1,3,4-thiadiazole in 5 ml of water, the reaction mixture was heated under nitrogen for 3 hours to 60°-65° C. After cooling, to 0° C, the pH-value was adjusted to 4 by means of 2N-hydrochloric acid, the precipitate was filtered off with suction and washed with water and acetone. 0.58 g of 3-[(5-methyl-1,3,4-thiadiazole-2-yl)-thiomethyl]-7-[4-amidinophenoxyacetamido]-Δ3-cephem-4-carboxylic acid melting at 208° to 210° C (decomposition) were obtained.

EXAMPLE 47

In a manner analogous to that of Example 46, there was obtained from 0.90 g of 7-(4-amidino-phenoxyacetamido)-cephalosporanoic acid and 0.30 g of 2-methyl-5-mercapto-1,3,4-oxadiazole-, 0.80 g of 3-[(5-methyl-1,3,4-oxadiazole-2-yl)-thiomethyl]-7-[4-amidinophenoxyacetamido)-Δ3-cephem-4-carboxylic acid melting at 240° to 245° C (decomposition).

EXAMPLE 48

In a manner analogous to that of Example 46, there was obtained from 0.90 g of 7-(4-amidino-phenoxyacetamido)-cephalosporanoic acid and 0.39 g of 2-phenyl-5-mercapto-1,3,4-oxadiazole, 0.75 g of 3-[(5-phenyl-1,3,4-oxadiazole-2-yl)-thiomethyl]-7-(4-amidino-phenoxyacetamido)-Δ3-cephem-4-carboxylic acid. After dissolution and re-precipitation from a mixture of dimethyl sulfoxide and acetone at 228° to 232° C with decomposition.

EXAMPLE 49

In a manner analogous to that of Example 44, there was obtained from 0.90 g of 7-(4-amidino-phenoxyacetamido)-cephalosporanoic acid and 0.29 g of 2-amino-5-mercapto-1,3,4-thiadiazole, 0.73 g of 3-[(5-amino-1,3,4-thiadiazole-2-yl)-thiomethyl]-7-(4-amidinophenoxyacetamido)-Δ3-cephem-4-carboxylic acid melting at 245° to 248° C (decomposition).

EXAMPLE 50

1.46 g of 7-[4-(1,4,5,6-tetrahydropyrimide-2-yl)-phenoxyacetamido]-cephalosporanoic acid were reacted in a manner analogous to that of Example 44 with 0.65 g of 2-phenyl-5-mercapto-1,3,4-thiadiazole. After cooling of the reaction mixture, the oil that had precipitated was decanted off and triturated with acetone, whereupon it crystallized. The solution which had been decanted off was adjusted to pH 4, whereupon a further quantity of the substance precipitated. In total, 1.08 g of 3-[(5-phenyl-1,3,4-thiadiazole-2-yl)-thiomethyl]-7-[1,4,5,6-tetrahydro pyrimide-2-yl)-pnenoxyacetamido]-Δ3-cephem-4-carboxylic acid melting at 155° to 160° C (decomposition).

EXAMPLE 51

In a manner analogous to that of Example 50, there was obtained from 1.46 g of 7-[4-(1,4,5,6-tetrahydropyrimide-2-yl)-phenoxyacetamido]-cephalosporanoic acid and 0.59 g of 2-phenyl-5-mercapto-1,3,4-oxadiazole, 1.16 g of 3-[(5-phenyl-1,3,4-oxadiazole-2-yl)-thiomethyl]-7-[4-(1,4,5,6-tetrahydropyrimide-2-yl)-phenoxyacetamido]-Δ3-cephem-4-carboxylic acid melting at 170° to 175° C (decomposition) was obtained.

EXAMPLE 52

In a manner analogous to that of Example 44, there was obtained from 1.37 g of 7-[4-(imidazoline-2-yl)-phenyl-acetamido]-cephalosporanoic acid and 0.65 g of 2-phenyl-5-mercapto-1,3,4-thiadiazole, 1.20 g of 3-[(5-phenyl-1,3,4-thiadiazole-2-yl)-thiomethyl]-7-[4-(imidazoline-2-yl)-phenylacetamido]-Δ3-cephem-4-carboxylic acid melting at 185° to 190° C (decomposition).

EXAMPLE 53

In a manner analogous to that of Example 50, there was obtained from 1.37 g of 7-[4-(imidazoline-2-yl)-phenylacetamido]-cephalosporanoic acid and 0.58 g of 2-n-propyl-5-mercapto-1,3,4-thiadiazole, 0.73 g of 3-[(5-n-propyl-1,3,4-thiadiazole-2-yl)-thiomethyl]-7-[4-imidazoline-2-yl)-phenylacetamido]-Δ3-cephem-4-carboxylic acid melting at 175° to 180° C (decomposition).

EXAMPLE 54

In a manner analogous to that of Example 44, there was obtained from 1.3 g of 7-(4-amidino-phenylacetamido)-cephalosporanoic acid and 0.60 g of 2-n-butyl-5-mercapto-1,3,4-oxadiazole, 1.05 g of 3-[(5-n-butyl-1,3,4-oxadiazole-2-yl)-thiomethyl]-7-(4-amidino-phenylacetamido)-Δ3-cephem-4-carboxylic acid melting at 247° to 252° C (decomposition).

EXAMPLE 55

In a manner analogous to that of Example 44, there was obtained from 1.3 g of 7-(4-amidinophenylacetamido)-cephalosporanoic acid and 0.62 g of 2-n-butyl-5-mercapto-1,3,4-thiadiazole, 1.20 g of 3-[(5-n-butyl-1,3,4-thiadiazole-2-yl)-thiomethyl]-7-(4-amidinophenylacetamido)-Δ3-cephem-4-carboxylic acid melting at 200° to 204° C (decomposition).

EXAMPLE 56

In a manner analogous to that of Example 44, there was obtained from 1.3 g of 7-(4-amidinophenylacetamido)-cephalosporanoic acid and 0.71 g of 2-phenyl-5-mercapto-1,3,4-oxadiazole, 1.3 g of 3-[(5-phenyl-1,3,4-oxadiazole-2-yl)-thiomethyl]-7-(4-amidinophenylacetamido)-Δ3-cephem-4-carboxylic acid melting at 213° to 217° C (decomposition).

EXAMPLE 57

In a manner analogous to that of Example 44, there was obtained from 1.30 g of 7-(4-amidinophenylacetamido)-cephalosporanoic acid and 0.78 g of 2-phenyl-5-mercapto-1,3,4-thiadiazole, 1.36 g of 3-[(5-phenyl-1,3,4-thiadiazole-2-yl)-thiomethyl]-7-(4-amidinophenylacetamido)-Δ3-cephem-4-carboxylic acid melting at 228° to 230° C (decomposition).

EXAMPLE 58

In a manner analogous to that of Example 44, there was obtained from 1.30 g of 7-(4-amidinophenylacetamido)-cephalosporanoic acid and 0.64 g of 2-n-propyl-5-mercapto-1,3,4-thiadiazole, 1.15 g of 3-[(5-n-propyl-1,3,4-thiadiazole-2-yl)-thiomethyl]-7-(4-amidinophenylacetamido)-Δ3-cephem-4-carboxylic acid melting at 238° to 243° C (decomposition).

EXAMPLE 59

In a manner analogous to that of Example 44, there was obtained from 1.3 g of 7-(4-amidinophenylacetamido)-cephalosporanoic acid and 0.53 g of 2-amino-5-mercapto-1,3,4-thiadiazole, 0.85 g of 3-[(5-amino-1,3,4-thiadiazole-2-yl)-thiomethyl]-7-(4-amidinophenylacetamido)-Δ3-cephem-4-carboxlic acid melting at 254° to 260° C (decomposition).

EXAMPLE 60

In a manner analogous to that of Example 44, there was obtained from 1.30 g of 7-(4-amidinophenylacetamido)-cephalosporanoic acid and 0.60 g of 2-methyl-5-mercapto-1,3,4-oxadiazole, 1.25 g of 3-[(5-methyl-1,3,4-oxadiazole-2-yl)-thiomethyl]-7-(4-amidinophenylacetamido)-Δ3-cephem-4-carboxylic acid melting at 250° to 253° C (decomposition).

EXAMPLE 61

In a manner analogous to that of Example 44, there was obtained from 1.30 g of 7-(amidinophenylacetamido)-cephalosporanoic acid and 0.41 g of 2-mercapto-1,3,4-oxadiazole, 1.27 g of 3-[(1,3,4-oxadiazole-2-yl)-thiomethyl]-7-(4-amidinophenylacetamido)-Δ3-cephem-4-carboxylic acid melting at 252° to 256° C (decomposition).

EXAMPLE 62

In a manner analogous to that of Example 46, there was obtained from 7[4-(1,4,5,6-tetrahydropyrimide-2-yl)-phenoxyacetamido]-cephalosporanoic acid and 0.39 g of 2-mercepto-1,3,4-thiadiazole, 0.67 g of 3-[(1,3,4-thiadiazole-2-yl)-thiomethyl]-7-(1,4,5,6-tetrahydropyrimide-2-yl)-phenoxyacetamido]-Δ3-cephem-4-carboxylic acid melting at 175° to 180° C (decomposition).

EXAMPLE 63

In a manner analogous to that of Example 44, there was obtained from 1.8 g of 7-(4-amidinophenoxyacetamido)-cephalosporanoic acid and 0.60 g of 2-mercapto-1,3,4-thiadiazole, 1.21 g of 3-[(1,3,4-thiadiazole-2-yl)-thiomethyl]-7-(4amidinophenoxyacetamido)-Δ3-cephem-4-carboxylic acid melting at 180° to 185° C.

EXAMPLE 64

In a manner analogous to that of Example 46, there was obtained from 0.90 g of 7-(4-amidinophenoxyacetamido-)-cephalosporanoic acid and 0.29 g of 4-methyl-5-mercapto-1,3-thiazole, 0.71 g of 3-[(4-methyl-1,3-thiazole-2-yl)-thiomethyl]-7-(4-amidinophenoxyacetamido)-Δ3-cephem-4-carboxylic acid melting at 230° to 235° C (decomposition).

EXAMPLE 65

0.90 g of 7-(4-amidinophenoxy)-cephalosporanoic acid was reacted with 0.41 g of 2-phenyl-5-mercapto-1,3,4-thiadiazole in a manner analogous to that of Example 44. When the reaction was completed, the reaction mixture was allowed to stand overnight after addition of acetone, the granular precipitate was filtered off with suction and washed with acetone. 0.94 g of 3-[(5-phenyl-1,3,4-thiadiazole-2-yl)-thiomethyl]-7-(4-amidinophenoxyacetamido)-Δ3-cephem-4-carboxylic acid melting at 198° to 200° C was obtained.

EXAMPLE 66

0.90 g of 4-(4-amidinophenoxy)-cephalosporanoic acid was reacted in a manner analogous to that of Example 44 with 0.33 g of 2-n-butyl-5-mercapto-1,3,4-oxadiazole. After cooling to 0° C, a viscous product was obtained which, after decantation of the solution, was washed with water and then stirred with acetone. The granular substance so obtained was filtered off with suction, washed with acetone and dried under reduced pressure. 0.85 g of 3-[(5-n-butyl-1,3,4-oxadiazole-2-yl)-thiomethyl]-7-(4-amidinophenoxyacetamido)-Δ3-cephem-4-carboxylic acid melting at 195° to 200° C (decomposition) was obtained.

EXAMPLE 67

In a manner analogous to that of Example 66, there were obtained from 1.8 g of 7-(4-amidinophenoxy)-cephalosporanoic acid and 0.80 g of 2-n-butyl-5-mercapto-1,3,4-thiadiazole, 1.65 g of 3-[(5-n-butyl-1,3,4-thiadiazole-2-yl)-thiomethyl]-7-(4-amidinophenoxyacetamido)-Δ3-cephem-4-carboxylic acid melting at 200° to 205° C (decomposition).

EXAMPLE 68

In a manner analogous to that of Example 66, there was obtained from 1.35 g of 7-(4-amidinophenoxy)-cephalosporanoic acid and 0.48 g of 2-n-propyl-5-mercapto-1,3,4-thiadiazole, 1.15 g of 3-[(5-n-propyl-1,3,4-thiadiazole-2-yl)-thiomethyl]-7-(4-amidinophenoxyacetamido)-Δ3-cephem-4-carboxylic acid melting at 212° to 216° C (decomposition).

EXAMPLE 69

A solution of 1.42 g of 7-[4-(1,4,5,6-tetrahydropyrimide-2-yl)-phenylacetamido]-cephalosporanoic acid in 30 ml of water was combined with 0.80 g of the sodium salt of 2-mercapto-4-methylmercapto-6-phenyl-1,3,5-triazine and heated, under nitrogen, for 3 hours at 65° C. The reaction mixture was cooled, the precipitate was filtered off with suction, washed with water and stirred for some time with 50 ml of acetone. The residue was filtered off with suction and washed with ether and hexane. 0.98 g of 3-[(4-methylmercapto-6-phenyl-1,3,5-triazine-2-yl)-thiomethyl]-7-[4-(1,4,5,6-tetrahydropyrimide-2-yl)-phenyl-acetamido]-Δ3-cephem-4-carboxylic acid melting at 206° to 208° C (decomposition) was obtained.

EXAMPLE 70

In a manner analogous to that of Example 50, there was obtained from 1.37 g of 7-(4-imidazoline-2-yl)-phenylacetamido]-cephalosporanoic acid and 0.47 g of 2-mercapto-1,3,4-thiadiazole, 0.90 g of 3-[(1,3,4-thiadiazole-2-yl)-thiomethyl]-7-[4-(imidazoline-2-yl)phenylacetamido]-Δ3-cephem-4-carboxylic acid melting at 170° to 173° C (decomposition).

EXAMPLE 71

In a manner analogous to that of Example 50, there was obtained from 1.4 g of 7-[4-(1,4,5,6-tetrahydropyrimide-2-yl)-phenylacetamido]-cephalosporanoic acid and 0.55 g of 1-phenyl-1-H-5-mercaptotetrazole, 0.81 g of 3-[(1-phenyl-1-H-tetrazole-5-yl)-thiomethyl]-7-[4-(1,4,5,6-tetrahydropyrimide-2-yl)-phenyl-acetamido]-Δ3-cephem-4-carboxylic acid melting at 170° to 173° C (decomposition) was obtained.

EXAMPLE 72

In a manner analogous to that of Example 44, there was obtained from 0.80 g of 7-(4-amidino-phenylacetamido)-cephalosporanoic acid and 0.28 g of 2-mercapto-pyridine, 1.00 g of 3-[(pyride-2-yl)-thiomethyl]-7-(4-amidino-phenylacetamido)-Δ3-cephem-4-carboxylic acid melting at 277° to 281° C (decomposition).

EXAMPLE 73

A mixture of 0.95 g of 7-[4-(imidazoline-2-yl)-phenoxyacetamido]-cephalosporanoic acid in 15 ml of water and 2 ml of acetone was adjusted to pH 7 by means of sodium bicarbonate and after addition of 0.26 g of 5-mercapto-1,3,4-thiadiazole and 0.17 g of sodium bicarbonate in 5 ml of water heated to 70° C for 4 hours under nitrogen. After cooling to 0° C, the product that had precipitated was decanted off and the residue was triturated with acetone, whereupon 1.245 g of 3-[(3-1,3,4,5-thiadiazole-2-yl)-thiomethyl]-7-[4-(imidazoline-2-yl)-phenoxyacetamido]-Δ3-cephem-4-carboxylic acid melting at 198° to 200° C (decomposition) were obtained. The solution that had been decanted off was adjusted to pH 4 and evaporated to dryness. The residue was dissolved in 20 ml of dimethyl sulfoxide and the filtrate was added dropwise, while cooling with ice, to 250 ml of acetone. The precipitate was filtered off with suction, washed with acetone and dried under reduced pressure, whereupon further 0.63 g of 3-[(1,3,4-thiadiazole-2-yl)-thiomethyl]-7-[4-(imidazoline-2-yl)-phenoxyacetamido]-Δ3-cephem-4-carboxylic acid melting at 198° to 200° C (decomposition) was obtained.

EXAMPLE 74

In a manner analogous to that of Example 73, there was obtained from 0.95 g of 7-[4-(imidazoline-2-yl)-phenoxyacetamido]-cephalosporanoic acid and 0.26 g of 2-methyl-5-mercapto-1,3,4-oxadiazole a total of 0.82 g of 3-[(5-methyl-1,3,4-oxadiazole-2-yl)-thiomethyl]-7-[4-(imidazoline-2-yl)-phenoxyacetamido]-Δ3-cephem-4-carboxylic acid melting at 205° to 211° C (decomposition).

EXAMPLE 75

In a manner analgous to that of Example 73, there was obtained from 0.95 g of 7-[4-(imidazoline-2-yl)-phenoxyacetamido]-cephalosporanoic acid and 0.29 g of 2-methyl-5-mercapto-1,3,4-thiadiazole, 0.64 g of 3-[(5-methyl-1,3,4-thiadiazole-2-yl)-thiomethyl]-7-[4-(imidazoline-2-yl)-phenoxyacetamido]-Δ3-cephem-4-carboxylic acid melting at 180° to 185° C (decomposition).

EXAMPLE 76

A mixture of 1.46 g of 7-[4-(1,4,5,6-tetrahydropyrimide-2-yl)-phenoxyacetamido]-cephalosporanoic acid in 200 ml of water and 2 ml of acetone was adjusted with sodium bicarbonate to pH 7 and, after addition of 0.38 g of 2-methyl-5-mercapto-1,3,4-oxadiazole and 0.26 g of sodium bicarbonate in 10 ml of water, was heated for 4 hours to 70° C under nitrogen. After cooling to 0° C, the whole was adjusted to pH 4, filtered and the filtrate was concentrated to dryness. The residue was triturated with ethanol, the solid product was filtered off with suction and dissolved in dimethyl-sulfoxide. The filtrate was added dropwise to acetone, while cooling with ice, and the product that had precipitated was filtered off with suction, washed with acetone and dried under reduced pressure. 0.87 g of 3-[(5-methyl-1,3,4-oxadiazole-2-yl)-thiomethyl]-7-[4-(1,4,5,6-tetrahydropyrimide-2-yl)-phenoxy-acetamido]-Δ3-cephem-4-carboxylic acid melting at 210° to 215° C (decomposition) was obtained.

EXAMPLE 77

1.89 g of 7-[4-(1,4,5,6-tetrahydropyrimide-2-yl)-phenylacetamido]-cephalosporanoic acid were reacted as described in Example 76 with 0.80 g of 2-n-butyl-5-mercapto-1,3,4-thiadiazole. After concentration of the filtrate to dryness, there was obtained an oil which was washed with water and dried subsequently under a high vacuum. The residue was then dissolved and re-precipitated from a mixture of dimethyl sulfoxide and acetone. 0.96 g of 3-[(5-n-butyl-1,3,4-thiadiazole-2-yl)-thiomethyl]-7-[4-(1,4,5,6-tetrahydropyrimide-2-yl)-phenylacetamido]-Δ3-cephem-4-carboxylic acid melting at 173° to 175° C (decomposition) was obtained.

EXAMPLE 78

A solution of 1.42 g of 7-[4-(1,4,5,6-tetrahydropyrimide-2-yl)-phenylacetamido]-cephalosporanoic acid in 20 ml of water and 2 ml of acetone was combined with 0.37 g of 2-methyl-5-mercapto-1,3,4-oxadiazole and 0.24 g of sodium bicarbonate in 5 ml of water and then heated for 4 hours to 70° C under nitrogen. After cooling, the solution was concentrated to dryness, the residue was dissolved in 20 ml of dimethyl sulfoxide, filtered and the filtrate was added dropwise, while cooling with ice, to 250 ml of acetone. The precipitate was filtered off with suction, washed with acetone and dried under reduced pressure. 1.28 g of 3-[(5 -methyl-1,3,4-oxadiazole-2-yl)-thiomethyl]-[4-(1,4,5,6-tetrahydropyrimide-2-yl)-phenylacetamido]-Δ3-cephem-4-carboxylic acid melting at 203° to 205° C (decomposition) was obtained.

EXAMPLE 79

In a manner analogous to that of Example 78, there was obtained from 1.42 g of 7-[4-(1,4,5-6-tetrahydropyrimide-2-yl)-phenylacetamido]-cephalosporanoic acid and 0.49 g of 2-n-propyl-5-mercapto-1,3,4-thiadiazole, 1.24 g of 3-[(5-n-propyl-1,3,4-thiadiazole-2-yl)-thiomethyl]-7-[4-(1,4,5,6-tetrahydropyrimide-2-yl)-phenylacetamido]-Δ3-cephem-4-carboxylic acid melting at 210° to 215° C (decomposition) was obtained.

EXAMPLE 80

In a manner analogous to that of Example 78, there was obtained from 1.42 g of 7-[4-(1,4,5,6-tetrahydropyrimide-2-yl)-phenylacetamido]-cephalosporanoic acid and 0.59 g of 2-phenyl-5-mercapto-1,3,4-thiadiazole, 1.34 g of 3-[(5-phenyl-1,3,4,-thiadiazole-2-yl)-thiomethyl]-7-[4-(1,4,5,6-tetrahydropyrimide-2-yl)-phenylacetamido]-Δ3-cephem-4-carboxylic acid melting at 210° to 220° C (decomposition).

EXAMPLE 81

In a manner analogous to Example 78, there was obtained from 1.42 g of 7-[4-(1,4,5,6-tetrahydropyrimide-2-yl)-phenylacetamido]-cephalosporanoic acid and 0.48 g of 2-n-butyl-5-mercapto-1,3,4-oxadiazole, 1.37 g of 3-[(5-n-butyl-1,3,4-oxadiazole-2-yl)-thiomethyl]-7-[4-(1,4,5,6-tetrahydropyrimide-2-yl)-phenylacetamido]-Δ3-cephem-4-carboxylic acid melting at 190° to 200° C (decomposition).

EXAMPLE 82

In a manner analogous to that of Example 78 there was obtained from 1.42 g of 7-[4-(1,4,5,6-tetrahydropyrimide-2-yl)-phenylacetamido]-cephalosporanoic acid and 0.44 g of 2-n-propyl-5-mercapto-1,3,4-oxadiazole, 1.20 g of 3-[(5-n-propyl-1,3,4-oxadiazole-2-yl)-thiomethyl]-7-[4-(1,4,5,6-tetrahydropyrimide-2-yl)-phenylacetamido-]-Δ3-cephem-4-carboxylic acid melting at 200° to 210° C (decomposition).

EXAMPLE 83

In a manner analogous to that of Example 78, there was obtained from 1.42 g of 7-[4-(1,4,5,6-tetrahydropyrimide-2-yl)-phenylacetamido]-cephalosporanoic acid and 0.54 g of 2-phenyl-5-mercapto-1,3,4-oxadiazole, 1.2 g of 3-[(5-phenyl-1,3,4-oxadiazole-2-yl)-thiomethyl]-7-[4-(1,4,5,6-tetrahydropyrimide-2-yl)-phenylacetamido]-Δ3-cephem-4-carboxylic acid melting at 210° to 220° C (decomposition).

EXAMPLE 84

0.58 g of N,N'-dicyclohexyl-carbodiimide in 10 ml of DMF was added dropwise to a solution that had been cooled to 0° C of 1.67 g of 3-[(1,3,4-thiadiazole-2-yl)-thiomethyl]-7-amino-Δ3-cephem-4-carboxylic acid benzhydryl ester-p-toluene-sulfonate (melting point 151° to 152° C) and 0.51 g of 4-(imidazoline-2-yl)-phenylacetic acid in 25 ml of DMF. The whole was allowed to stand for 1 hour at 0° C and overnight at about 20° C and filtered and the product was precipitated from the filtrate by means of ether. 1.2 g of 3-[(1,3,4-thiadiazole-2-yl)-thiomethyl]-7-[4-(imidazoline-2-yl)-phenylacetamido]-Δ3-cephem-4-carboxylic acid-benzhydryl ester-p-toluene sulfonate in the form of an amorphous solid was obtained, which compound was found to decompose at about 95° C. Infrared spectrum (KBr):

β-Lactam at 1775, ester at 1720 and acyl at 1660 $cm^{-1}$.

EXAMPLE 85

In a manner analogous to that of Example 44, there was obtained from 0.95 g of 7-[4-(1,4,5,6-tetrahydropyrimide-2-yl)-phenylacetamido]-cephalosporanoic acid and 0.37 g of 2-mercaptobenzothiazole, 0.90 g of 3-[benzothiazole-2-yl-thiomethyl]-7-[4-(1,4,5,6-tetrahydropyrimide-2-yl)-phenylacetamido]-Δ3-cephem-4-carboxylic acid melting at 200° to 203° C (decomposition).

EXAMPLE 86

In a manner analogous to that of Example 44, there was obtained from 1.41 g of 7-[4-(1,4,5,6-tetrahydropyrimide-2-yl)-phenylacetamido]-cephalosporanoic acid and 0.40 g of 2-mercapto-2-thiazoline, 0.8 g of 3-[2-thiazoline-2-yl-thiomethyl]-7-[4-(1,4,5,6-tetrahydropyrimide-2-yl)-phenyl-acetamido]-Δ3-cephem-4-carboxylic acid melting at 220° to 225° C (decomposition).

EXAMPLE 87

In a manner analogous to that of Example 36 b, there was obtained from 1.16 g of 4-(1,4,5,6-tetrahydropyrimide-2-yl)-phenylacetyl chloride (from Example 11 a) and 1.38 g of 3-[(1-methyl-1H-tetrazole-5-yl)-thiomethyl]-7-amino-Δ3-cephem-4-carboxylic acid, 0.48 g of 3-[(1-methyl-1H-tetrazole-5-yl)-thiomethyl]-7-[4-(1,4,5,6-tetrahydropyrimide-2-yl)-phenylacetamido]-Δ3-cephem-4-carboxylic acid melting at 220° C (decomposition).

EXAMPLE 88

In a manner analogous to that of Example 36 b, 0.65 g of 4-(2-imidazolinyl-phenyl)-acetyl chloride-hydrochloride and 3-[2-thiazoline-2-yl-thiomethyl]-7-amino-Δ3-cephem-4-carboxylic acid were reacted. After 1 hour at −2° C and 2 hours at 25° C, the solution was filtered, adjusted to pH 3.5 and the precipitate was filtered off with suction. After washing with water and acetone, there was obtained 0.6 g of 3-[2-thiazoline-2-yl-thiomethyl]-7-[4-(imidazoline-2-yl)-phenyl-acetamido]-Δ3-cephem-4-carboxylic acid melting at 240° to 245° C (decomposition).

EXAMPLE 89

In the same manner as that of Example 44, there was obtained from 1.3 g of 7-(4-amidino-phenylacetamido)-cephalosporanoic acid and 0.31 g of 5-mercapto-1-methyl-1-H-tetrazole, 0.8 g of 3-[(1-methyl-1H-tetrazole-5-yl)-thiomethyl]-7-[4-amidino-phenylacetamido]-Δ3-cephem-4-carboxylic acid melting at 215° C to 220° C (decomposition).

EXAMPLE 90

In a manner analogous to that of Example 44, there was obtained from 1.30 g of 4-(4-amidino-phenylacetamido)-cephalosporanoic acid and 0.40 g of 2-mercapto-2-thiazoline, 0.85 g of 3-[2-thiazoline-2-yl-thiomethyl]-7-[4-amidino-phenylacetamido]-Δ3-cephem-4-carboxylic acid melting at 235° to 240° C (decomposition).

EXAMPLE 91

In a manner analogous to that of Example 44, there was obtained from 1.30 g of 7-(4-amidino-phenylacetamido)-cephalosporanoic acid and 0.59 g of 2-mercapto-quinoline, 0.85 g of 3-quinoline[-2-yl-thiomethyl]-7-[4-amidino-phenyl-acetamido]-Δ3-cephem-4-carboxylic acid melting at 250° C (decomposition.

EXAMPLE 92

In a manner analogous to that of Example 44, there was obtained from 1.30 g of 7-(4-amidino-phenyl-acetamido)-cephalosporanoic acid and 0.55 g of 2-mercapto-benzothiazole, 1.13 g of 1.13 g of 3-[benzothiazole-2-yl-thiomethyl]-7-[4-amidino-phenylacetamido]-Δ3-cephem-4-carboxylic acid melting at 250° to 255° C (decomposition).

EXAMPLE 93

In a manner analogous to that of Example 46, there were reacted 1.46 of 7-[4-(1,4,5,6-tetrahydropyrimide-2-yl)-phenoxyacetamido]-cephalosporanic acid and 0.31 g of 5-mercapto-1-methyl-1-H-tetrazole. After cooling to 0° C, the whole was acidified to pH 4, the precipitate was filtered off with suction and washed with acetone. The filtrate was concentrated to dryness, the residue was dissolved in dimethyl-sulfoxide and, after filtration, a further amount of final product was precipitated from the solution with a mixture of acetone and ether. A total of 0.7 g of 3-[(1-methyl-1-H-tetrazol-5-yl)-thiomethyl]-7-[4-(1,4,5,6-tetrahydropyrimide-2-yl)-phenoxyacetamido-]-Δ3-cephem-4-carboxylic acid melting at 210° C (decomposition) was obtained.

EXAMPLE 94

The process of Example 20 was repeated with the difference that 0.28 g of 2-mercapto-triazole was used instead of the 2-mercapto-thiazole. 0.8 g of 3-[(triazole-2-yl)-thiomethyl]-7-[4-(1,4,5,6-tetrahydropyrimide-2-yl)-phenylacetamido]-Δ3-cephem-4-carboxylic acid melting at about 225° C (decomposition) was obtained.

EXAMPLE 95

The process of Example 20 was repeated with the difference that 0.36 g of 2-mercapto-5-ethyl-triazole was used instead of the 2-mercapto-thiazole. 1.25 g of 3-[(5-ethyl-triazole-2-yl)-thiomethyl]-7-[4-(1,4,5,6-tetrahydro-pyrimide-2-yl)-phenylacetamido]-Δ3-cephem-4-carboxylic acid melting at about 230° C (decomposition) was obtained.

EXAMPLE 96

The process of Example 20 was repeated with the difference that 0.35 g of 2-thiouracil was used instead of the 2-mercaptothiazole. 1.0 g of 3-[(4-hydroxy-pyrimide-2-yl)-thiomethyl]-7-[4-(1,4,5,6-tetrahydropyrimide-2-yl)-phenylacetamido]-Δ3-cephem-4-carboxylic acid melting at about 220° C (decomposition) was obtained.

EXAMPLE 97

The process of Example 20 was repeated with the difference that 0.31 g of 4-mercapto-pyridine was used instead of the 2-mercapto-thiazole. 0.82 g of 3-(4-pyridyl-thiomethyl)-7-[4-(1,4,5,6-tetrahydropyrimide-2-yl)-phenylacetamido]-Δ3-cephem-4-carboxylic acid melting at about 220° C (decomposition) was obtained.

EXAMPLE 98

The process of Example 13 was repeated with the difference that 0.38 g of 4,6-dimethyl-2-mercapto-pyrimidine was used instead of the 3-phenyl-5-mercapto-1,2,4-thiadiazole. 0.65 g of 3-[4,6-dimethyl-pyrimide-2-yl)-thiomethyl]-7-[4-(1,4,5,6-tetrahydropyrimide-2-yl)-phenylacetamido]-Δ3-cephem-4-carboxylic acid melting at 232° C (decomposition) was obtained.

EXAMPLE 99

The process of Example 13 was repeated with the difference that 0.59 g of 2-mercapto-5-phenyl-4H-1,3,4-thiadiazine was used instead of the 3-phenyl-5-mercapto-1,2,4-thiadiazole. 0.81 g of 3-[(5-phenyl-4H-1,3,4-thiadiazine-2-yl)-thiomethyl]-7[4-(1,4,5,6-tetrahydropyrimide-2-yl)-phenylacetamido]-Δ3-cephem-4-carboxylic acid melting at about 240° C (decomposition) was obtained.

EXAMPLE 100

The process of Example 20 was repeated with the difference that 0.32 g of 3-mercapto-4-amino-4H-1,2,4-triazole was used instead of the 2-mercapto-thiazole. 1.22 g of 3-[(4-amino-4H-1,2,4-triazole-3-yl)-thiomethyl]-7-[4-(1,4,5,6-tetrahydropyrimide-2-yl)-phenylacetamido]-Δ3-cephem-4-carboxylic acid melting at about 235° C (decomposition) was obtained.

EXAMPLE 101

The process of Example 20 was repeated with the difference that 0.36 g of 3-mercapto-4-amino-5-methyl-1,2,4-triazole was used instead of the 2-mercapto-thiazole. 1.4 g of 3-[(4-amino-5-methyl-1,2,4-triazole-3-yl)-thiomethyl]-7-[4-(1,4,5,6-tetrahydropyrimide-2-yl)-phenylacetamido]-Δ3-cephem-4-carboxylic acid melting at about 225° C (decomposition) was obtained.

EXAMPLE 102

The process of Example 20 was repeated with the difference that 0.35 g of 2-mercapto-4-methyl-pyrimidine was used instead of the 2-mercapto-thiazole. 1.1 g of 3-[(4-methyl-pyrimide-2-yl)-thiomethyl]-7-[4-(1,4,5,6-tetrahydropyrimide-2-yl)-phenylacetamido]-Δ3-cephem-4-carboxylic acid melting at about 200° C (decomposition) was obtained.

EXAMPLE 103

The process of Example 13 was repeated with the difference that 0.49 g of 2-phenyl-5-mercapto-oxadiazole was used instead of the 3-phenyl-5-mercapto-1,2,4-thiadiazole. 0.9 g of 3-[(5-phenyl-1,3,4-oxadiazole-2-yl)-thiomethyl]-7-[4-(1,4,5,6-tetrahydropyrimide-2-yl)-phenylacetamido]-Δ3-cephem-4-carboxylic acid melting at about 200° C (decomposition) was obtained.

EXAMPLE 104

The process of Example 20 was repeated with the difference that 0.40 g of 3-mercapto-4-amino-5-ethyl-1,2,4-triazole was used instead of the 2-mercapto-thiazole. 1.25 g of 3-[(4-amino-5-ethyl-1,2,4-triazole-3-yl)-thiomethyl]-7-[4-(1,4,5,6-tetrahydropyrimide-2-yl)-phenylacetamido-]-Δ3-cephem-4-carboxylic acid melting at about 230° C (decomposition) was obtained.

EXAMPLE 105

The process of Example 13 was repeated with the difference that 0.43 g of 2-mercapto-5-nitro-pyridine was used instead of the 3-phenyl-5-mercapto-1,2,4-thiadiazole. 0.9 g of 3-[(5-nitropyridine-2-yl)-thiomethyl]-7-[4-(1,4,5,6-tetrahydropyrimide-2-yl)-phenylacetamido]-Δ3-cephem-4-carboxylic acid melting at about 230° C (decomposition) was obtained.

EXAMPLE 106

The process of Example 13 was repeated with the difference that 0.40 g of 4,5-dimethyl-thiazole was used instead of the 3-phenyl-5-mercapto-1,2,4-thiadiazole. 0.5 g of 3-[(4,5-dimethylthiazole-2-yl)-thiomethyl]-7-[4-(1,4,5,6-tetrahydropyrimide-2-yl)-phenylacetamido]-Δ3-cephem-4-carboxylic acid melting at about 189° C (decomposition) was obtained.

EXAMPLE 107

The process of Example 20 was repeated with the difference that 0.41 g of 2-mercapto-pyridine-N-oxide was used instead of the 2-mercapto-thiazole. 1.1 g of 3-[(1-oxido-2-pyridyl)-thiomethyl]-7-[4-(1,4,5,6-tetrahydropyrimide-2-yl)-phenylacetamido]-Δ3-cephem-4-carboxylic acid melting at about 160° C was obtained.

EXAMPLE 108

The process of Example 20 was repeated with the difference that 0.36 g of 3-methyl-5-mercapto-1,2,4-thiadiazole was used instead of the 2-mercapto-thiazole. 1.4 g of 3-[(3-methyl-1,2,4-thiadiazole-5-yl)-thiomethyl]-7-[4-(1,4,5,6-tetrahydropyrimide-22-yl)-phenylacetamido]-Δ3-cephem-4-carboxylic acid melting at about 205° C (decomposition) was obtained.

EXAMPLE 109

The process of Example 13 was repeated with the difference that 0.45 g of 2-mercapto-benzoxazole was used instead of the 3-phenyl-5-mercapto-1,3,4-thiadiazole-, 0.7 g of 3-[(benzoxazole-2-yl)-thiomethyl]-7-[4-(1,4,5,6-tetrahydropyrimide-2-yl)-phenylacetamido]-Δ3-cephem-4-carboxylic acid melting at about 185° C was obtained (decompositioned.

EXAMPLE 110

The process of Example 13 was repeated with the difference that 0.45 g of 2-mercapto-benzothiazole was used instead of the 3-phenyl-5-mercapto-1,2,4-thiadiazole. 0.4 g of 3-[(benzothiazole-2-yl)-thiomethyl]-7-[4-(1,4,5,6-tetrahydropyrimide-2-yl)-phenylacetamido]-Δ3-cephem-4-carboxylic acid melting at about 173° (decomposition) was obtained.

EXAMPLE 111

In a manner analogous to that of Example 13, 2.29 g of 7-[4-imidazoline-2-yl)-phenyl-acetamido]-cephalosporanoic acid were reacted with 0.95 g of 2-mercapto-4-tert.butyl-thiazole. 0.83 g of 3-[(4-tert.butyl-thiazole-2-yl)-thiomethyl]-7-[-4-(imidazoline-2-yl)-phenylacetamido]-Δ3-cephem-4-carboxylic acid melting at 183° C (decomposition) was obtained.

EXAMPLE 112

In a manner analogous to that of Example 13, 2.29 g of 7-[(4-imidazoline-2-yl)-phenylacetamido]-cephalosporanoic acid were reacted with 0.8 g of 2-mercapto-4-isopropyl-thiazole. 1.1 g of 3-[(4-isopropyl-thiazole-2-yl)-thiomethyl]-7-[4-(imidazoline-2-yl)-phenylacetamido]-Δ3-cephem-4-carboxylic acid melting at about 183° C (decomposition) was obtained.

EXAMPLE 113

In a manner analogous to that of Example 13, 2.29 g of 7-[(4-imidazoline-2-yl)-phenyl-acetamido]-cephalosporanoic acid were reacted with 0.9 g of 2-mercapto-4n-butyl-thiazole. 1.2 g of 3-[(4-n-butyl-thiazole-2-yl)-thiomethyl]-7-[4-imidazoline-2-yl)-phenylacetamido]-Δ3-cephem-4-carboxylic acid melting at about 182° C (decomposition) was obtained.

EXAMPLE 114

In a manner analogous to that of Example 13, 2.29 g of 7-[(4-imidazoline-2-yl)-phenyl-acetamido]-cephalosporanoic acid were reacted with 0.8 g of 2-mercapto-4n-propyl-thiazole. 1.0 g of 3-[(4-n-propyl-thiazole-2-yl)-thiomethyl]-7-[4-(imidazoline-2-yl)-phenylacetamido]-Δ3-cephem-4-carboxylic acid melting at about 175° C (decomposition) was obtained.

EXAMPLE 115

In a manner analogous to that of Example 13, 2.29 g of 7-[(4-imidazoline-4-yl)-phenyl-acetamido]-cephalosporanoic acid were reacted with 0.7 g of 2-mercapto-4-ethyl-thiazole. 0.9 g of 3-[(4-ethyl-thiazole-2-yl)-thiomethyl]-7-[4-(imidazoline-2-yl)-phenylacetamido]-Δ3-cephem-4-carboxylic acid melting at about 185° C (decomposition) was obtained.

EXAMPLE 116

In a manner analogous to that of Example 13, 2.29 g of 7-[(4-imidazoline-2-yl)-phenylacetamido]-cephalosporanoic acid were reacted with 1.0 g of 2-mercapto-5-phenyl-1,3,4-oxadiazole. 1.2 g of 3-[(5-phenyl-1,3,4-oxadiazole-2-yl)-thiomethyl]-7-[4-(imidazoline-2-yl)-phenylacetamido]-Δ3-cephem-4-carboxylic acid melting at about 205° C (decomposition) was obtained.

EXAMPLE 117

In a manner analogous to that of Example 13, 2.29 g of 7-[(4-imidazoline-2-yl)-phenyl-acetamido]-cephalosporanoic acid were reacted with 1.1 g of 2-mercapto-4-phenyl-thiazole. 1.8 g of 3-[(4-phenyl-thiazole-2-yl)-thiomethyl]-7-[4-(imidazoline-2-yl)-phenylacetamido]-Δ3-cephem-4-carboxylic acid melting at about 200° C (decomposition) were obtained.

EXAMPLE 118

In a manner analogous to that of Example 13, 2.29 g of 7-[(4-imidazoline-2-yl)-phenylacetamido]-cephalosporanoic acid were reacted with 0.9 g of 2-mercapto-benzothiazole. 1.3 g of 3-[(benzothiazole-2-yl)-thiomethyl]-7-[4-(imidazoline-2-yl)-phenylacetamido]-Δ3-cephem-4-carboxylic acid melting at about 185° C (decomposition) was obtained.

EXAMPLE 119

In a manner analogous to that of Example 13, 2.29 g of 7-[(4-imidazoline-2-yl)-phenyl-acetamido]-cephalosporanoic acid were reacted with 0.9 g of 2-mercapto-benzoxazole. 1.3 g of 3-[(benzoxazole-2-yl)-thiomethyl]-7-[(imidazoline-2-yl)-phenylacetamido]-Δ3-cephem-4-carboxylic acid melting at about 195° C (decomposition) was obtained.

EXAMPLE 120

In a manner analogous to that of Example 1 b) there was obtained from 1.30 g of 4-(2-imidazolinyl)-phenylacetyl chloride-hydrochloride (preparation cf. Example 10 a) and 1.79 g of 3-(5-ethyl-1,3,4-thiadiazole-2-yl)-thiomethyl-7-amino-Δ3-cephem-4-carboxylic acid the acylation product which, upon combination with 2N-hydrochloric acid, yielded 1.92 g of the hydrochloride of 3-[(5-ethyl-1,3,4-thiadiazole-2-yl)-thiomethyl]-7-[(4-(-2- imidazolinyl)-phenylacetamido]-Δ3-cephem-4-carboxylic acid melting at 107° to 110° C (decomposition).

EXAMPLE 121

In a manner analogous to that of Example 1 b, there were obtained from 2.18 g of 4-(1,4,5,6-tetrahydropyrimide-2yl)-phenylacetyl chloride-hydrochloride (preparation cf. Example 11 a) and 2.86 g of 3-(5-ethyl-1,3,4-thiadiazole-2-yl)-thiomethyl-7-amino-Δ3-cephem-4-carboxylic acid, 3.25 g of 3-[(5-ethyl-1,3,4-thiadiazole-2-yl)-thiomethyl]-7-[4-(1,4,5,6-tetrahydropyrimide-2-yl)-phenylacetamido]-Δ3-cephem-4-carboxylic acid melting at 178° to 180° C (decomposition).

EXAMPLE 122

In a manner analogous to that of Example 1 b, there were obtained from 1.17 g of 4-amidinophenylacetyl chloride-hydrochloride (preparation cf. Example 1 a) and 1.79 g of 3-(5ethyl-1,3,4-thiadiazole-2-yl)-thiomethyl-7-amino-Δ3-cephem-4-carboxylic acid, 1.94 g of 3-[(5-ethyl-1,3,4-thiadiazole-2-yl)-thiomethyl]-7-(4-amidino-phenylacetamido)-Δ3-cephem-4-carboxylic acid melting at 197° to 199° C (decomposition).

The same compound was obtained with a good yield when reacting in a manner analogous to Example 44, 1.73 g of 7-(4-amidinophenylacetamido)-cephalosporanoic acid with 0.64 g of 2-mercapto-5-ethyl-1,3,4-thiadiazole.

EXAMPLE 123

In a manner analogous to the method described in Example 10, there were obtained from 820 mg of 7-[4-(imidazoline-2-yl)-phenylacetamido]-cephalosporanoic acid and 230 mg of 1-methyl-2-mercapto-imidazole by heating for 7 hours to 50° – 55° C, 270 mg of 3-[(1-methylimidazole-2-yl)-thiomethyl]-7-[4-(imidazoline-2-yl)-phenylacetamido]-Δ 3-cephem-4-carboxylic acid melting at 185° to 190° C (decomposition).

EXAMPLE 124

In a manner analogous to that of Example 44, there were obtained from 820 mg of 4-[4-(imidazoline-2-yl)-phenylacetamido]-cephalosporanoic acid and 210 mg of 2-mercapto-1,3,4-oxadiazole, after 8 hours at 45° C, 320 mg of 3-[(1,3,4-oxadiazole-2-yl)-thiomethyl]-7-[4-(imidazoline-2-yl)-phenylacetamido]-Δ3-cephem-4-carboxylic acid melting at 220° to 223° C (decomposition).

EXAMPLE 125 a. A suspension of 2.9 g of 4-(imidazoline-2-yl)-2-methoxphenoxy-acetic acid in 15 ml of benzene and 20 ml of thionyl chloride was combined with 0.2 ml of dimethylformamide and stirred for 6 hours at 75° C, then filtered and the residue was washed with benzene and di-isopropyl ether. 2.5 g of 4-(imidazoline-2-yl)-2-methoxy-phenoxyacetyl chloride-hydrochloride melting at 200° C were obtained.

b. 2.33 g of 7-aminocephalosporanoic acid (7-ACS) were dissolved in a solution of 2.1 g of sodium bicarbonate in a mixture of 75 ml of water and 7.5 ml of acetone and combined at −5° C with 2.5 g of 4-(imidazoline-2-yl)-2-methoxy-phenoxyacetyl chloride-hydrochloride in portions. After 1 hour at 0° C, the whole was acidified to pH 4, the solid substance that had precipitated was filtered off and the reaction mixture was subsequently concentrated to dryness. The organic components were dissolved with 25 ml of dimethyl-sulfoxide and this solution was dropped into 350 ml of acetone. The cream-coloured precipitate that had separated was filtered off and washed with acetone. 2.72 g of 7-[4-(imidazoline-2-yl)-2-methoxyphenoxyacetamido]-cephalosporanoic acid melting at 195° to 200° C (decomposition) were obtained.

c. In a manner analogous to that of Example 44, there were obtained from 1.08 g of 7-[4-(imidazoline-2-yl)-2-methoxy-phenoxyacetamido]-cephalosporanoic acid and 260 mg of 2-mercapto-1,3,4-thiadiazole, 760 mg of 3-[(1,3,4-thiadiazole-2-yl)-thiomethyl]-7-[4-(imidazoline-2-yl)-2-methoxy-phenoxyacetamido]-Δ3-cephem-4-carboxylic acid melting at 198°–202° C (decomposition).

EXAMPLE 126

In a manner analogous to that of Example 44, there were obtained from 1.08 g of 7-[4-(imidazoline-2-yl)-2-methoxyphenoxyacetamido]-cephalosporanoic acid and 260 mg of 2-mercapto-1,3,4-thiadiazole, 760 mg of 3-[(1,3,4-thiadiazole-2-yl)-thiomethyl]-7-[4-(imidazoline-2-yl)-2-methoxy-phenoxyacetamido]-Δ3-cephem-4-carboxylic acid melting at 198° to 202° C (decomposition).

EXAMPLE 126

In a manner analogous to that of Example 44, there were obtained from 820 mg of 7-[4-(imidazoline-2-yl)-2-methoxy-phenoxyacetamido]-cephalosporanoic acid and 240 mg of 5-methyl-2-mercapto-1,3,4-thiadiazole, 440 mg of 3-[(5-methyl-1,3,4-thiadiazole-2-yl)-thiomethyl]-7-[4-(imidazoline-2-yl)-2-methoxyphenoxyacetamido]-Δ3-cephem-4-carboxylic acid melting at 208° to 209° C.

EXAMPLE 127 a. A suspension of 6.15 g of 4-amidino-2-methoxy-phenoxyacetic acid in 60 ml of benzene and 10 ml of thionyl chloride was combined with 0.2 ml of dimethylformamide and heated. After 2 hours at 65° C, a well stirrable, colorless suspension had formed. The precipitate was isolated, washed with benzene and di-isopropylether and dried. 6.5 g of 4-amidino-2-methoxy-phenoxyacetyl chloride-hydrochloride melting at 155° to 156° C (decomposition) were obtained.

b. In the same manner as described in Example 1 b, 6.5 g of 4-amidino-2-methoxy-phenoxyacetyl chloride-hydrochloride were reacted with 6.3 g of 7-aminocephalosporanoic acid. After completion of the addition of the acid chloride, 9.51 g of 7-(4-amidino-2-methoxy-phenoxyacetamido)-cephalosporanoic acid melting at 237° to 239° crystallized.

c. In a manner analogous to Example 44, there were obtained from 1.43 g of 7-(4-amidino-2-methoxy-phenoxyacetamido)-cephalosporanoic acid and 390 mg of 2-mercapto-1,3,4-thiadiazole, 650 mg of 3-[(1,3,4-thiadiazole-2-yl)-thiomethyl]-7-(4-amidino-2-methoxyphenoxyacetamido-Δ3-cephem-4-carboxylic acid melting at 185° to 190° C (decomposition).

EXAMPLE 128

The process of Example 127 c was repeated with 440 mg of 5-methyl-2-mercapto-1,3,4-thiadiazole. 620 mg of 3-[(5-methyl-1,3,4-thiadizole-2-yl)-thiomethyl]-7(4-amidino-2-methoxy-phenoxy-acetamido)-Δ3-cephem-4-carboxylic acid melting at 215° to 220° C (decomposition) were obtained.

EXAMPLE 129

The process of Example 127 c was repeated with 390 mg of 2-mercapto-1,3-thiazole. 780 mg of 3-[(1,3-thiazole-2-yl)thiomethyl]-7-(4-amidino-2-methoxy-phenoxyacetamido)-Δ3-cephem-4-carboxylic acid melting at 210° to 215° C (decomposition) was obtained.

EXAMPLE 130

The process of Example 127 c was repeated with 430 mg of 4-methyl-2-mercapto-1,3-thiazole. 740 mg of 3-[(4-methyl-1,3-thiazole-2-yl)-thiomethyl]-7-(4-amidino-2-methoxy-phenoxyacetamido)-Δ3-cephem-4-carboxylic acid melting at 200° to 205° C (decomposition) were obtained.

We claim:
1. An acylamino-cephem-carboxylic acid of the formula

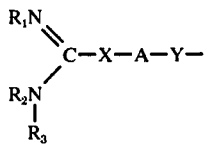

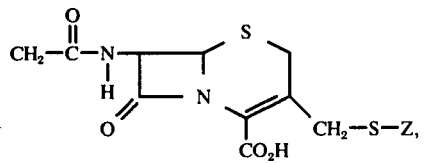

and physiologically tolerated salts and physiologically tolerated esters thereof, wherein $R_1$, $R_2$, and $R_3$, taken alone, are hydrogen or alkyl having 1 to 8 carbon atoms; $R_1$ and $R_2$, taken together, or $R_2$ and $R_3$, taken together, are alkylene having 2 to 5 carbon atoms, alkylene having 2 to 5 carbon atoms substituted with alkyl having 1 to 4 carbon atoms or with alkyl having 1 to 4 carbon atoms interrupted by an oxygen atom, or are alkylene having 2 to 5 carbon atoms which is ortho- or spiro-fused to 5- or 6-membered cycloalkyl or oxacycloalkyl; X is a single bond or —NH—; A is phenylene, thienylene, or phenylene or thienylene substituted with alkyl having 1 to 4 carbon atoms, alkoxy having 1 to 4 carbon atoms, or halogen; Y is a single bond or —O—; and Z is is a heterocyclic ring selected from the group consisting of thienyl, furyl, pyrrolyl, imidazolyl, pyrazolyl, thiazolyl, thiazolinyl, oxazolyl, oxazolinyl, isoxazolyl, triazolyl, thiadiazolyl, oxadiazolyl, tetrazolyl thiatriazolyl, pyridyl, pyrimidyl, pyrazinyl, pyradiazinyl, thiazinyl, triazinyl, thiadiazinyl, imidazolinyl and tetrahydropyrimidyl, or Z is such a heterocyclic ring substituted by at least one member selected from the group consisting of alkyl having 1 to 15 carbon atoms, cyclopentyl, cyclohexyl, lower alkoxy, lower alkenyl, lower alkylmercapto, lower alkoxycarbonyl, lower alkoxycarbonylamino, amino, lower alkylamino, hydroxy, nitro, phenyl, lower alkoxyphenyl, halophenyl, hydroxyphenyl, aminophenyl, lower alkylphenyl, cetylphenyl, nitrophenyl, biphenylyl, pyridyl, methylpyridyl, furyl, naphthyl, quinolyl, isoquinolyl, thienyl, 2-thiazolyl, 2-pyrrolyl, 4-imidazolyl, 5-pyrazolyl, 4-isoxazolyl, and lower alkyl having 1 to 4 carbon atoms substituted by phenyl, phenoxy, lower alkoxy, or lower alkoxycarbonyl, or Z is such a heterocyclic ring ortho-fused to a benzene ring, or Z is pyridyl-N-oxide or pyridazinyl-N-oxide.

2. A compound as claimed in claim 1, which is 3-[(1,3,4-Thiadiazole-2-yl)-thiomethyl]-7-(4-amidino-phenylacetamido)-Δ3-cephem-4-carboxylic acid.

3. A compound as claimed in claim 1, which is 3-[(5-Methyl-1,3,4-thiadiazole-2-yl)-thiomethyl]-7-(5-amidino-thienylacetamido)-Δ3-cephem-4-carboxylic acid.

4. A compound as claimed in claim 1, which is 3-[(1,3,4-Thiadiazole-2-yl)-thiomethyl]-7-(5-amidino-thienyl-acetamido)-Δ3-cephem-4-carboxylic acid.

5. A compound as claimed in claim 1, which is 3-[(Thiadiazole-2-yl)-thiomethyl]-7-(4-amidino-phenylacetamido)-Δ-3-cephem-4-carboxylic acid.

6. A compound as claimed in claim 1, which is 3-[(4-Methyl-thiazole-2-yl)-thiomethyl]-7-(4-amidino-phenylacetamido)-Δ3-cephem-4-carboxylic acid.

7. A compound as claimed in claim 1, which is 3-[(5-Methyl-1,3,4-thiadiazole-2-yl)-thiomethyl]-7-(4-guanidino-phenylacetamido)-Δ3-cephem-4-carboxylic acid.

8. A compound as claimed in claim 1, which is 3-[(4-Methyl-thiazole-2-yl)-thiomethyl]-7-(4-guanidino-phenyl-acetamido)-Δ3-cephem-4-carboxylic acid.

9. A compound as claimed in claim 1, which is 3-[(Thiazole-2-yl)-thiomethyl]-7-(4-guanidino-phenylacetamido)-Δ3-cephem-4-carboxylic acid.

10. A compound as claimed in claim 1, which is 3-[(1,3,4-thiadiazole-2-yl)-thiomethyl]-7-(4-guanidinophenyl-acetamido)-Δ3-cephem-4-carboxylic acid.

11. A compound as claimed in claim 1, which is 3-[(4-Methyl-thiazole-2-yl)-thiomethyl]-7-[4-(imidazoline-2-yl)-phenylacetamido]-Δ3-cephem-4-carboxylic acid.

12. A compound as claimed in claim 1, which is 3-[(5-Methyl-1,3,4-thiadiazole-2-yl)-thiomethyl]-7-[4-(1,4,5,6-tetrahydro-pyrimide-2-yl)-phenylacetamido]-Δ3-cephem-4-carboxylic acid.

13. A compound as claimed in claim 1, which is

3-[(5-Methyl-1,3,4-thiadiazole-2-yl)-thiomethyl]-7-[4-(imidazoline-2-yl)-phenylacetamido]-Δ3-cephem-4-carboxylic acid.

14. A compound as claimed in claim 1, which is 3-[(4-Methyl-thiazole-2-yl)-thiomethyl]-7-[4-(1,4,5,6-tetrahydropyrimide-2-yl)-phenylacetamido]-Δ3-cephem-4-carboxylic acid.

15. A compound as claimed in claim 1, which is 3-[(5-Methyl-1,2,4-triazole-3-yl)-thiomethyl]-7-[4-(1,4,5,6-tetrahydropyrimide-2-yl)-phenylacetamido]-Δ3-cephem-4-carboxylic acid.

16. A compound as claimed in claim 1, which is 3-[(5-Methyl-1,2,4-triazole-3-yl)-thiomethyl]-7-(4-amidinophenylacetamido)-Δ3-cephem-4-carboxylic acid.

17. A compound as claimed in claim 1, which is 3-[(1,2,4-Triazole-3-yl)-thiomethyl]-7-(4-amidino-phenylacetamido)-Δ3-cephem-4-carboxylic acid.

18. A compound as claimed in claim 1, which is 3-[(1,3,4-Thiadiazole-2-yl)-thiomethyl]-7-[4-(1,4,5,6-tetrahydropyrimide-2-yl)-phenylacetamido]-Δ3-cephem-4-carboxylic acid.

19. A compound as claimed in claim 1, which is 3-[(5-Methyl-1,3,4-thiadiazole-2-yl)-thiomethyl]-7-(4-amidiono-phenylacetamido)-Δ3-cephem-4-carboxylic acid.

20. A compound as claimed in claim 1, which is 3-[(5-Methyl-1,3,4-thiadiazole-2-yl)-thiomethyl]-7-[4-(1,4,5,6-tetrahydropyrimide-2-yl)-phenoxyacetamido]-Δ3-cephem-4-carboxylic acid.

21. A compound as claimed in claim 1, which is 3-[(5-Methyl-1,3,4-thiadiazole-2-yl)-thiomethyl]-7-(4-amidino-phenoxyacetamido)-Δ3-cephem-4-carboxylic acid hydrochloride.

22. A compound as claimed in claim 1, which is 3-[(5-n-Propyl-1,3,4-thiadiazole-2-yl)-thiomethyl]-7-[4-(imidazoline-2-yl)-phenoxyacetamido]-Δ3-cephem-4-carboxylic acid.

23. A compound as claimed in claim 1, which is 3-[(5-Methyl-1,3,4-oxadiazole-2-yl)-thiomethyl]-7-(4-amidino-phenoxyacetamido)-Δ3-cephem-4-carboxylic acid.

24. A compound as claimed in claim 1, which is 3-[(5-n-Propyl-1,3,4-oxadiazole-2-yl)-thiomethyl]-7-(4-amidino-phenylacetamido)-Δ3-cephem-4-carboxylic acid.

25. A compound as claimed in claim 1, which is 3-[(5-Methyl-1,3,4-thiadiazole-2-yl)-thiomethyl]-7-(4-amidino-phenoxyacetamido)-Δ3-cephem-4-carboxylic acid.

26. A compound as claimed in claim 1, which is 3-[(5-Phenyl-1,3,4-thiadiazole-2-yl)-thiomethyl]-7-[4-(imidazoline-2-yl)-phenylacetamido]-Δ3-cephem-4-carboxylic acid.

27. A compound as claimed in claim 1, which is 3-[(5-n-Propyl-1,3,4-thiadiazole-2-yl)-thiomethyl]-7-[4-(imidazoline-2-yl)-phenylacetamido]-Δ3-cephem-4-carboxylic acid.

28. A compound as claimed in claim 1, which is 3-[(5-n-Butyl-1,3,4-thiadiazole-2-yl)-thiomethyl]-7-(4-amidino-phenylacetamido-Δ3-cephem-4-carboxylic acid.

29. A compound as claimed in claim 1, which is 3-[(5-Phenyl-1,3,4-oxadiazole-2-yl)-thiomethyl]-7-(4-amidino-phenylacetamido)-Δ3-cephem-4-carboxylic acid.

30. A compound as claimed in claim 1, which is 3-[(5-n-Propyl-1,3,4-thiadiazole-2-yl)-thiomethyl]-7-(4-amidino-phenylacetamido)-Δ3-cephem-4-carboxylic acid.

31. A compound as claimed in claim 1, which is 3-[(5-Amino-1,3,4-thiadiazole-2-yl)-thiomethyl]-7-(4-amidino-phenylacetamido)-Δ3-cephem-4-carboxylic acid.

32. A compound as claimed in claim 1, which is 3-[(5-Methyl-1,3,4-oxadiazole-2-yl)-thiomethyl]-7-(4-amidino-phenylacetamido)-Δ3-cephem-4-carboxylic acid.

33. A compound as claimed in claim 1, which is 3-[(1,3,4-Thiadiazole-2-yl)-thiomethyl]-7-[4-(1,4,5,6-tetrahydropyrimide-2-yl)-phenoxyacetamido]-Δ3-cephem-4-carboxylic acid.

34. A compound as claimed in claim 1, which is 3-[(1,3,4-Thiadiazole-2-yl)-thiomethyl]-7-(4-amidonophenoxyacetamido)-Δ3-cephem-4-carboxylic acid.

35. A compound as claimed in claim 1, which is 3-[(1,3,4-Thiadiazole-2-yl)-thiomethyl]-7-[4-(imidazoline-2-yl)-phenoxyacetamido]-Δ3-cephem-4-carboxylic acid.

36. A compound as claimed in claim 1, which is 3-[(5-Methyl-1,3,4-oxadiazole-2-yl)-thiomethyl]-7-[4-(imidazoline-2-yl)-phenoxyacetamido]-Δ3-cephem-4-carboxylic acid.

37. A compound as claimed in claim 1, which is 3-[(5-Methyl-1,3,4-thiadiazole-2-yl)-thiomethyl]-7-[4-(imidazoline-2-yl)-phenoxyacetamido]-Δ3-cephem-4-carboxylic acid.

38. A compound as claimed in claim 1, which is 3-[(5-Methyl-1,3,4-oxadiazole-2-yl)-thiomethyl]-7-[4-(1,4,5,6-tetrahydropyrimide-2-yl)-phenoxyacetamido]-Δ3-cephem-4-carboxylic acid.

39. A compound as claimed in claim 1, which is 3-[(1-Methyl-1H-tetrazole-5-yl)-thiomethyl]-7-[4-(1,4,5,6-tetrahydropyrimide-2-yl)-phenylacetamido]-Δ3-cephem-4-carboxylic acid.

40. A compound as claimed in claim 1, which is 3-[(1-Methyl-1H-tetrazole-5-yl)-thiomethyl]-7-[4-amidinophenylacetamido]-Δ3-cephem-4-carboxylic acid.

41. A compound as claimed in claim 1, which is 3-[(Triazole-2-yl)-thiomethyl]-7-[4-(1,4,5,6-tetrahydropyrimide-2-yl)-phenylacetamido]-Δ3-cephem-4-carboxylic acid.

42. A compound as claimed in claim 1, which is 3-(4-Pyridylthiomethyl)-7-[4-(1,4,5,6-tetrahydropyrimide-2-yl)-phenylacetamido]-Δ3-cephem-4-carboxylic acid.

43. A compound as claimed in claim 1, which is 3-[4,6-Dimethyl-pyrimide-2-yl)-thiomethyl]-7-[4-(1,4,5,6-tetrahydropyrimide-2-yl)-phenylacetamido]-Δ3-cephem-4-carboxylic acid.

44. A compound as claimed in claim 1, which is 3-[(4,5-Dimethyl-thiazole-2-yl)-thiomethyl]-7-[4-(1,4,5,6-tetrahydropyrimide-2-yl)-phenylacetamido]-Δ3-cephem-4-carboxylic acid.

45. A compound as claimed in claim 1, which is 3-[(1-Oxido-2-pyridyl)-thiomethyl]-7-[4-(1,4,5,6-tetrahydropyrimide-2-yl)-phenylacetamido]-Δ3-cephem-4-carboxylic acid.

46. A compound as claimed in claim 1, which is 3-[(3-Methyl-1,2,4-thiadiazole-5-yl)-thiomethyl]-7-[4-(1,4,5,6-tetrahydropyrimide-2-yl)-phenylacetamido]-Δ3-cephem-4-carboxylic acid.

47. A compound as claimed in claim 1, which is

3-[(4-Isopropyl-thiazole-2-yl)-thiomethyl]-7-[4-(imidazoline-2-yl)-phenylacetamido]-Δ3-cephem-4-carboxylic acid.

48. A compound as claimed in claim 1, which is 3-[(4-n-Butyl-thiazole-2-yl)-thiomethyl]-7-[4-(imidazoline-2-yl)-phenylacetamido]-Δ3-cephem-4-carboxylic acid.

49. A compound as claimed in claim 1, which is 3-[(4-Ethylthiazole-2-yl)-thiomethyl]-7-[4-(imidazoline-2-yl)-phenylacetamido]-Δ3-cephem-4-carboxylic acid.

50. A compound as claimed in claim 1, which is 3-[(4-Phenylthiazole-2-yl)-thiomethyl]-7-[4-imidazoline-2-yl)-phenylacetamido]-Δ3-cephem-4-carboxylic acid.

51. A compound as claimed in claim 1, which is 3-[(Benzthiazole-2-yl)-thiomethyl]-7-[4-(imidazoline-2-yl)-phenylacetamido]-Δ3-cephem-4-carboxylic acid.

52. A compound as claimed in claim 1, which is 3-[(5-Ethyl-1,3,4-thiadiazole-2-yl)-thiomethyl]-7-[4-imidazoline-2-yl)-phenylacetamido]-Δ3-cephem-4-carboxylic acid.

53. A compound as claimed in claim 1, which is 3-[5-(Ethyl-1,3,4-thiadiazole-2-yl)-thiomethyl]-7-[4-(1,4,5,6-tetrahydropyrimide-2-yl)-phenylacetamido]-Δ3-cephem-4-carboxylic acid.

54. A compound as claimed in claim 1, which is 3-[5-(Ethyl-1,3,4-thiadiazole-2-yl)-thiomethyl]-7-(4-amidino-phenylacetamido)-Δ3-cephem-4-carboxylic acid.

55. The compound defined in claim 1, which is 3-[(1-methyl-1-H-tetrazole-5-yl)-thiomethyl]-7-[4-(2-imidazolinyl)-phenylacetamido]-Δ3-cephem-4-carboxylic acid.

56. The compound defined in claim 1, which is 3-[(1,3,4-thiadiazole-2-yl)-thiomethyl]-7-[4-imidazoline-2-yl)-phenylacetamido]-Δ3-cephem-4-carboxylic acid.

* * * * *

UNITED STATES PATENT AND TRADEMARK OFFICE
CERTIFICATE OF CORRECTION

PATENT NO. : 4,016,159
DATED : April 5, 1977
INVENTOR(S) Dieter Bormann et al.

It is certified that error appears in the above-identified patent and that said Letters Patent are hereby corrected as shown below:

Columns 41 and 42 the sixth compound, the hyphen (-) in column A should be in column X, the radical  in column Y should be in column A and the radical 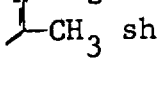 should be in column Z.

Signed and Sealed this sixteenth Day of August 1977

[SEAL]

Attest:

RUTH C. MASON
Attesting Officer

C. MARSHALL DANN
Commissioner of Patents and Trademarks